(12) United States Patent
Aoki

(10) Patent No.: US 10,145,679 B2
(45) Date of Patent: Dec. 4, 2018

(54) THREE-DIMENSIONAL SHAPE MEASURING DEVICE AND THREE-DIMENSIONAL SHAPE MEASURING METHOD

(71) Applicant: FUJITSU LIMITED, Kawasaki-shi, Kanagawa (JP)

(72) Inventor: Takahiro Aoki, Kawasaki (JP)

(73) Assignee: Fujitsu Limited, Kawasaki (JP)

( * ) Notice: Subject to any disclaimer, the term of this patent is extended or adjusted under 35 U.S.C. 154(b) by 27 days.

(21) Appl. No.: 14/966,960

(22) Filed: Dec. 11, 2015

(65) Prior Publication Data

US 2016/0202047 A1    Jul. 14, 2016

(30) Foreign Application Priority Data

Jan. 8, 2015    (JP) .................. 2015-002698

(51) Int. Cl.

| | |
|---|---|
| *G01B 11/24* | (2006.01) |
| *G06T 7/00* | (2017.01) |
| *A61B 5/117* | (2016.01) |
| *G06K 9/20* | (2006.01) |
| *G06K 9/00* | (2006.01) |

(52) U.S. Cl.
CPC .............. *G01B 11/24* (2013.01); *A61B 5/117* (2013.01); *G06K 9/2027* (2013.01); *G06T 7/0053* (2013.01); *G06K 2009/00395* (2013.01); *G06T 2207/10028* (2013.01)

(58) Field of Classification Search
CPC .... A61B 5/117; G06K 9/00006; G01B 11/24; G06T 2207/10028; G06T 7/0053

USPC .................................................. 356/601–613
See application file for complete search history.

(56) References Cited

U.S. PATENT DOCUMENTS

| | | | |
|---|---|---|---|
| 2006/0290781 A1 | 12/2006 | Hama | |
| 2011/0313297 A1 | 12/2011 | Ishihara | |
| 2013/0242073 A1 | 9/2013 | Watanabe | |

FOREIGN PATENT DOCUMENTS

| | | |
|---|---|---|
| JP | 2007-10346 | 1/2007 |
| JP | 2010-220893 | 10/2010 |

OTHER PUBLICATIONS

Extended European Search Report dated Jun. 6, 2016 for corresponding European Patent Application No. 15199246.8, 5 pages.

(Continued)

*Primary Examiner* — Tri T Ton
(74) *Attorney, Agent, or Firm* — Fujitsu Patent Center

(57) ABSTRACT

A three-dimensional shape measuring device is provided that enables an accuracy in measuring a three-dimensional shape of a subject to be improved even when a relationship between a luminance value and a distance deviates from an ideal point light source model in which the luminance value is inversely proportional to the square of the distance. A biometric authentication device includes a coefficient setting unit that sets a coefficient that is an index of a power in a model expression for making a luminance value of a captured image be proportional to an inverse of the power of a distance from a light source to a measurement point of the luminance value according to a prescribed condition, and a three-dimensional shape measuring unit that measures the three-dimensional shape of the subject according to the luminance value of the captured image and the coefficient.

7 Claims, 20 Drawing Sheets

(56) References Cited

OTHER PUBLICATIONS

Prados, E. et al., "Shape From Shading: a well-posed problem?", Proceedings / 2005 IEEE Computer Society Conerence on Computer Vision and Pattern Recognition, CVPR 2005: [Jun. 20-25, 2005, San Diego, CA], IEEE, Piscataway, NJ, USA, vol. 2, Jun. 20, 2005, pp. 870-877, XP010817545.

Henrique, Carlos et al., "Towards 3D Reconstruction of Endoscope Images Using Shape from Shading," Computer Graphics and Image Processing, 2000, Proceedings XIII Brazili AN Symposium on Gramado, Brazil, Oct. 17, 2000, Los Alamitos, CA, USA, IEEE COMPUT. SOC, US, pp. 90-96, XP010521932.

Okatani, Takayuki et al., "Shape Reconstruction from an Endoscope Image by Shape from Shading Technique for a Point Light Source at the Projection Center," Computer Vision and Image Understanding, vol. 66, No. 2, May 1, 1997, pp. 119-131, Article No. IV970613, XP055155053.

R. Kimmel et al., "Global Shape from Shading", CVGIP: Image Understanding 1994 IEEE, pp. 120-125 (6 pages).

R. Zhang et al., "Shape from Shading: A Survey", IEEE PAMI (Transactions on Pattern Analysis and Machine Intelligence), vol. 21, No. 8, Aug. 1999, pp. 690-706 (17 pages).

E. Prados et al., "Shape from Shading: a well-posed problem?", INRIA, No. 5297, Aug. 2004, pp. 1-55 (58 pages).

Korean Office Action dated Jan. 26, 2017 for corresponding Korean Patent Application No. 10-2015-0181112, with English Translation, 9 pages.

Korean Office Action dated Jul. 28, 2017 for corresponding Korean Patent Application No. 10-2015-0181112, with English Translation, 6 pages.

Chinese Office Action dated Nov. 16, 2017 for corresponding Chinese Patent Application No. 201510958072.1, with English Translation, 19 pages.

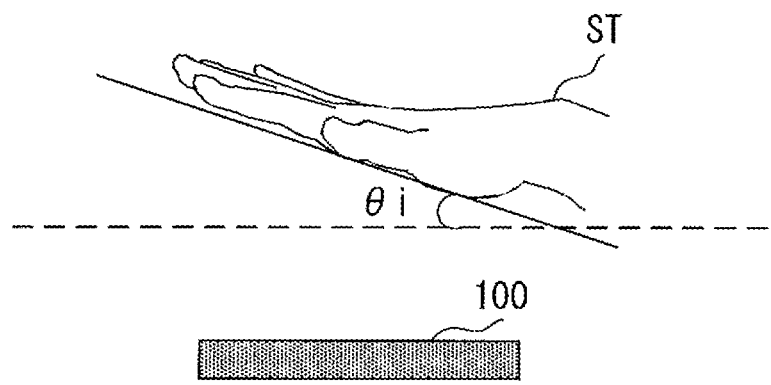
F I G. 1

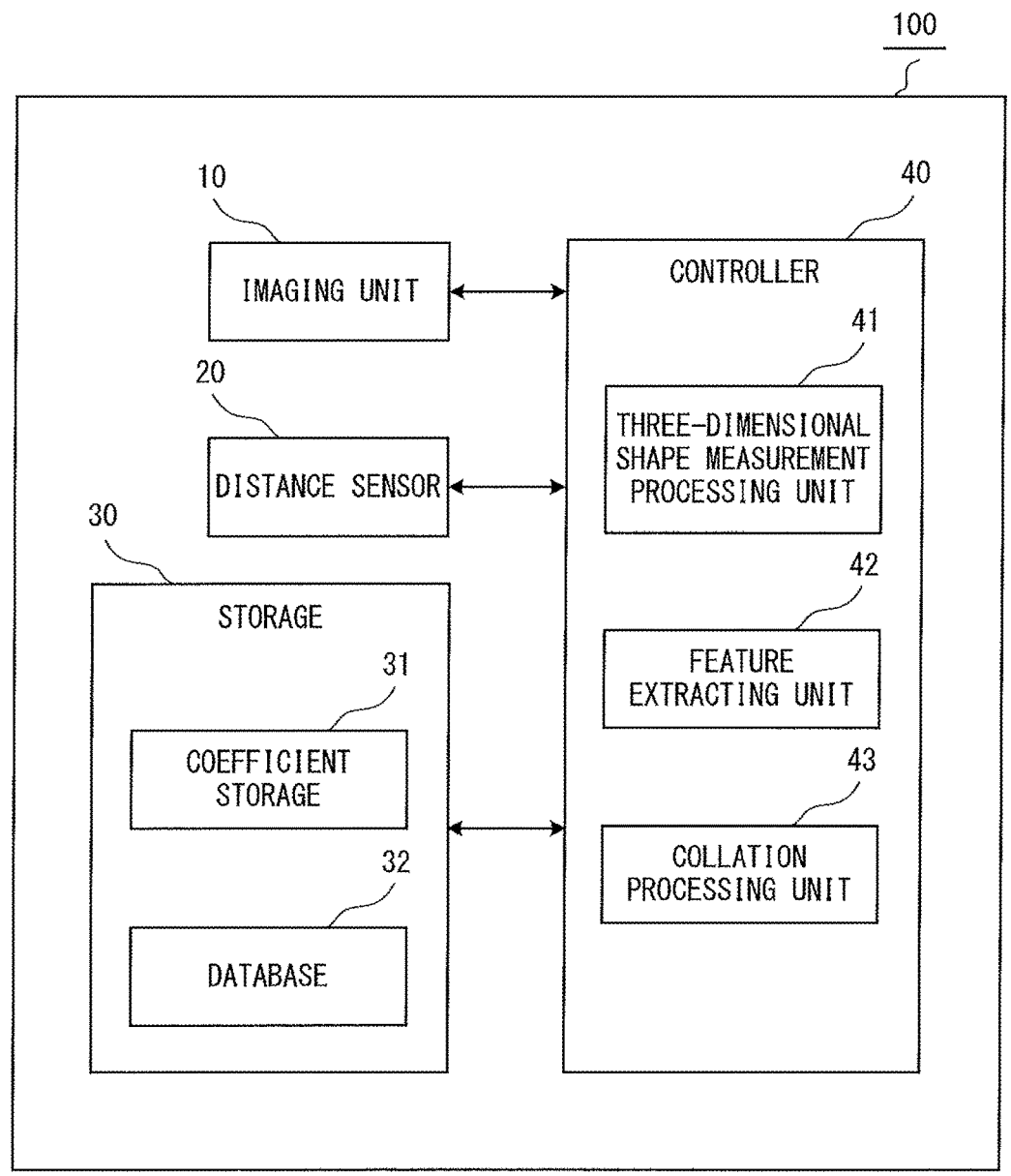
F I G. 6

| HEIGHT zr (mm) | α |
|---|---|
| zr1 | α(zr1) |
| zr2 | α(zr2) |
| zr3 | α(zr3) |
| zr4 | α(zr4) |
| ⋮ | ⋮ |

F I G. 7

| PIXEL X | SET OF COEFFICIENTS |
|---|---|
| X1 | A(X1), B(X1), C(X1) |
| X2 | A(X2), B(X2), C(X2) |
| X3 | A(X3), B(X3), C(X3) |
| X4 | A(X4), B(X4), C(X4) |
| ⋮ | ⋮ |

FIG. 10

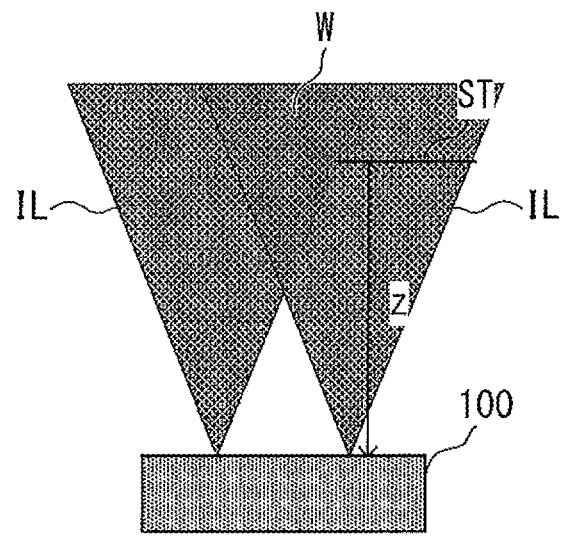
F I G. 14 A
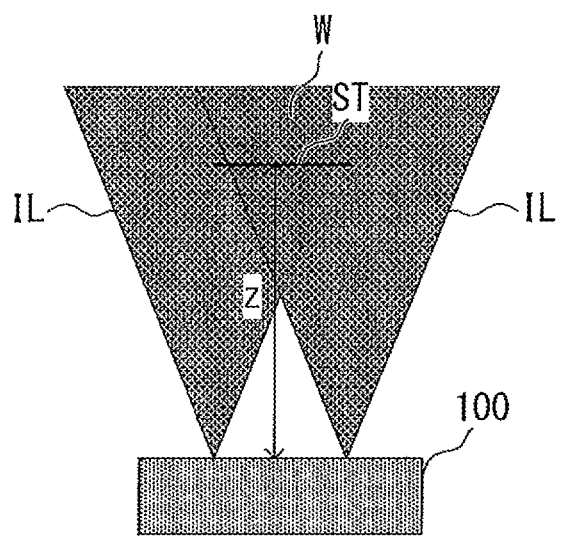
F I G. 14 B

| PIXEL X | α |
|---|---|
| X1 | α (X1) |
| X2 | α (X2) |
| X3 | α (X3) |
| X4 | α (X4) |
| ⋮ | ⋮ |

F I G. 1 7

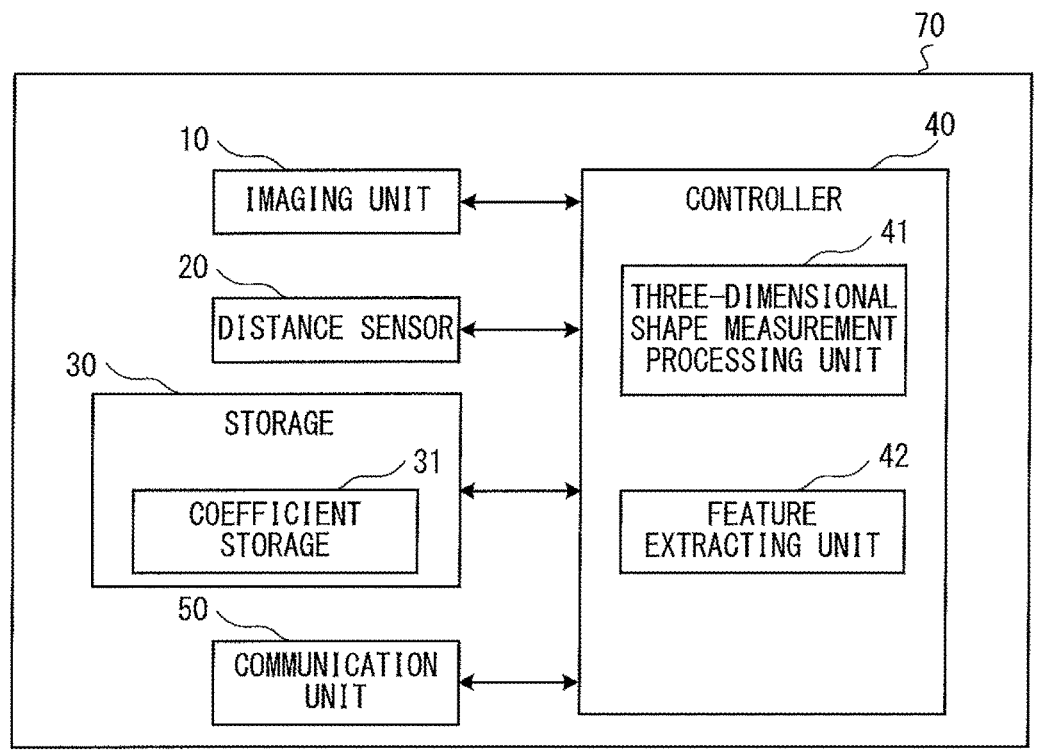
F I G. 1 9 A
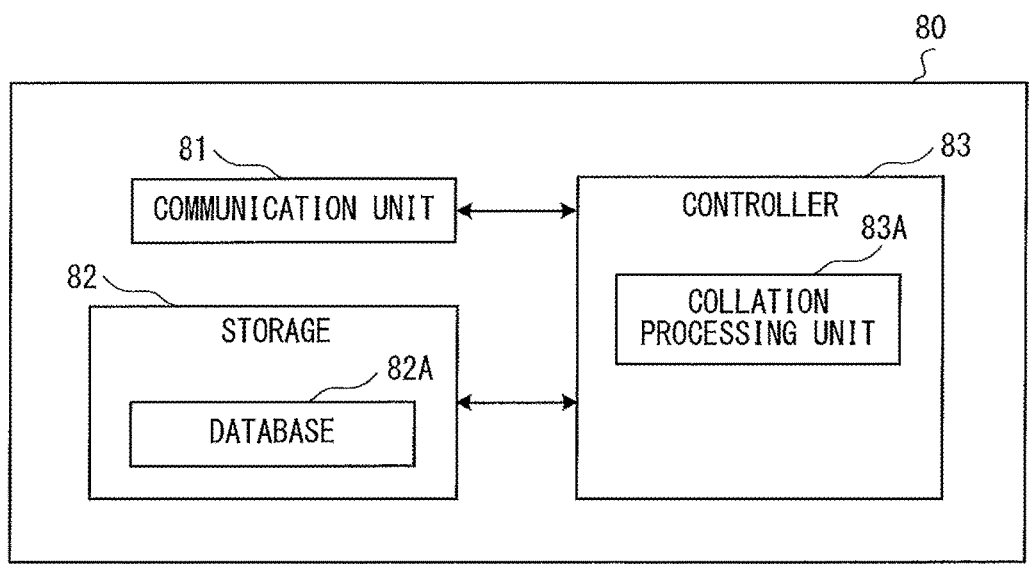
F I G. 1 9 B

THREE-DIMENSIONAL SHAPE MEASURING DEVICE AND THREE-DIMENSIONAL SHAPE MEASURING METHOD

CROSS-REFERENCE TO RELATED APPLICATION

This application is based upon and claims the benefit of priority of the prior Japanese Patent Application No. 2015-002698, filed on Jan. 8, 2015, the entire contents of which are incorporated herein by reference.

FIELD

The embodiments discussed herein are related to measuring of a three-dimensional shape.

BACKGROUND

A technology for measuring a three-dimensional shape of a subject on the basis of a captured image. Such a technology is employed in various technical fields. One example is a biometric authentication device such as a palm vein authentication device.

In the palm vein authentication device, when imaging biological data to be registered, a position of a hand, which is an example of the subject, is guided by a well-known guiding member or the like. However, there are cases in which a guiding member that guides the position of the hand when performing collation is not provided. When biological data of a hand that is not guided by a guiding member is imaged, a great difference may be generated between registration data and collation data due to a difference in the position of the hand, a tilt of the hand, or the like, and a success rate of personal authentication may be reduced.

One example of a method for solving the problem above is a method for measuring a posture such as a tilt of a hand and making correction to cancel deviation in the posture of the hand when performing collation. In this method, the posture of the hand can be detected by using a plurality of distance sensors so as to measure a distance from the respective distance sensors to a corresponding portion of the hand. However, in order to improve an accuracy in measuring the posture of the hand, a large number of distance sensors need to be used. Therefore, a cost for a biometric authentication device increases, and a size of the biometric authentication device also increases. Further, when the biometric authentication device has physical restrictions on a size or the like, it is very difficult to arrange the large number of distance sensors within the restrictions while maintaining a prescribed accuracy or more in measuring the posture of the hand.

Meanwhile, the Shape From Shading (SFS) technique for measuring a three-dimensional shape of a subject on the basis of an luminance value distribution of an image of a subject that is captured while the subject is being irradiated with illumination light is known (see, for example, Non-Patent Documents 1-3). By employing the SFS technique to measure a posture of a hand, distances from a light source to a large number of points can be measured without using a large number of distance sensors, and the posture of the hand can be detected with a higher accuracy.

[Patent Document 1] Japanese Laid-open Patent Publication No. 2007-10346

[Non-Patent Document 1] R. Kimmel et al., "Global Shape from Shading", CVGIP: Image Understanding, pp. 120-125, 1994

[Non-Patent Document 2] R. Zhang et al., "Shape from Shading: A Survey", IEEE PAMI (Transactions on Pattern Analysis and Machine Intelligence), Vol. 21, No. 8, pp. 690-706, August 1999

[Non-Patent Document 3] E. Prados et al., "Shape from Shading: a well-posed problem?", INRIA, No. 5297, pp. 1-55, August 2004

SUMMARY

A three-dimensional shape measuring device in one aspect of the invention is a three-dimensional shape measuring device that measures a three-dimensional shape of a subject included in a captured image, and includes a setting unit that sets a coefficient that is an index of a power in a model expression for making a luminance value of the captured image be proportional to an inverse of the power of a distance from a light source to a measurement point of the luminance value according to a prescribed condition, and a measuring unit that measures the three-dimensional shape of the subject according to the luminance value of the captured image and the coefficient.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 1 illustrates a tilt of a palm when performing authentication.

FIG. 6 is a functional block diagram illustrating an exemplary configuration of a biometric authentication device according to Embodiment 1.

FIG. 7 illustrates an example of information that is stored in a coefficient storage according to Embodiment 1 and that indicates a relationship between a height of a reference object and a coefficient α.

FIG. 10 illustrates an example of information in which a set of coefficients is associated with each of the pixels stored in a storage according to Embodiment 1.

FIGS. 14A and 14B are diagrams explaining a relationship between a position of a subject on a horizontal plane and a coefficient α according to Embodiment 2.

FIG. 17 illustrates an example of information in which a coefficient α is associated with each of the pixels stored in a coefficient storage according to Embodiment 2.

FIG. 19A is a functional block diagram illustrating an exemplary configuration of a biometric authentication sensor in a biometric authentication system according to Embodiment 4, and FIG. 19B is a functional block diagram illustrating an exemplary configuration of a server computer.

DESCRIPTION OF EMBODIMENTS

In a conventional SFS technique disclosed, for example, in Non-Patent Document 3, it is often assumed that an illumination intensity is inversely proportional to the square of a distance between a subject and a light source. More specifically, when a distance between a position that corresponds to a point X on a subject of a captured image and a light source is D(X), a luminance value I(X) at the point X is assumed to be obtained by the following expression 1. In expression 1, θi is an angle formed by a sight line vector of a camera and a normal vector of the subject, and $I_0$ is a constant.

$$I(X) = I_0 \frac{\cos\theta i}{D(X)^2} \quad (1)$$

Expression 1 for calculating the luminance value I(X) is a calculation expression in a case in which a light source is an ideal point light source, because the luminance value I(X) decreases according to $(1/D(X)^2)$. On the other hand, in an actual device such as a biometric authentication device, the luminance value I(X) is not always proportional to $(1/D(X)^2)$ due to the existence of a plurality of light sources, the influence of internal reflection, or the like.

In particular, a biometric authentication device corresponds to a proximity optical system in which an imaging device is close to a subject. As an example, in a palm vein authentication device, an authentication distance (a distance between an image sensor and a subject) is assumed to be a very short distance of about 5 cm. In such a proximity optical system, the luminance value I(X) often greatly deviates from the ideal point light source model, and there is a problem wherein, when the SFS technique is employed to measure a posture of a hand, a large error is generated. In particular, there is an advantage wherein, as a size (principally, a surface area) of a sensor of a biometric authentication device increases, distribution of an illumination intensity (a luminance value) becomes almost uniform, but deviation from a point light source model becomes great, and an error increases.

Embodiments are described below with reference to the drawings.

Embodiment 1

Figure 1:
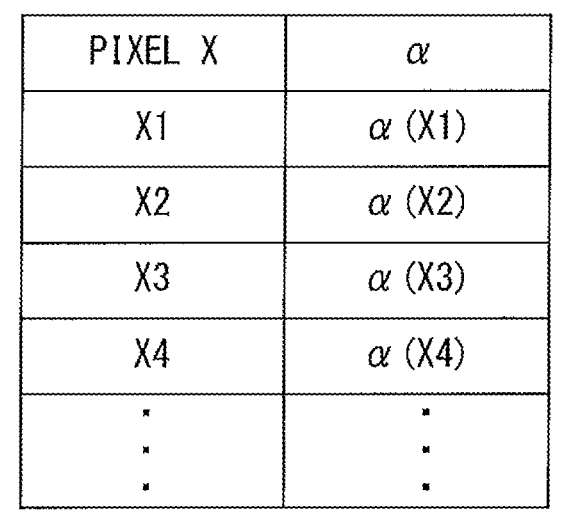

FIG. 1 illustrates a tilt of a palm ST when performing authentication. A biometric authentication device 100 according to Embodiment 1 is a palm vein authentication device in which a target for biometric authentication is the palm veins, and is an example of a three-dimensional shape measuring device. It is assumed that the biometric authentication device 100 according to Embodiment 1 is not provided with a guiding member that guides a position of a hand. Therefore, when performing authentication, the palm ST may fail to be horizontal to the biometric authentication device 100 and may tilt, as illustrated in FIG. 1. FIG. 1 illustrates an example in which an angle that is formed by a horizontal line (a broken line in FIG. 1) orthogonal to an optical axis of the biometric authentication device 100 (optical axes of a light source and an image sensor) and the palm ST is θi.

Figure 2:
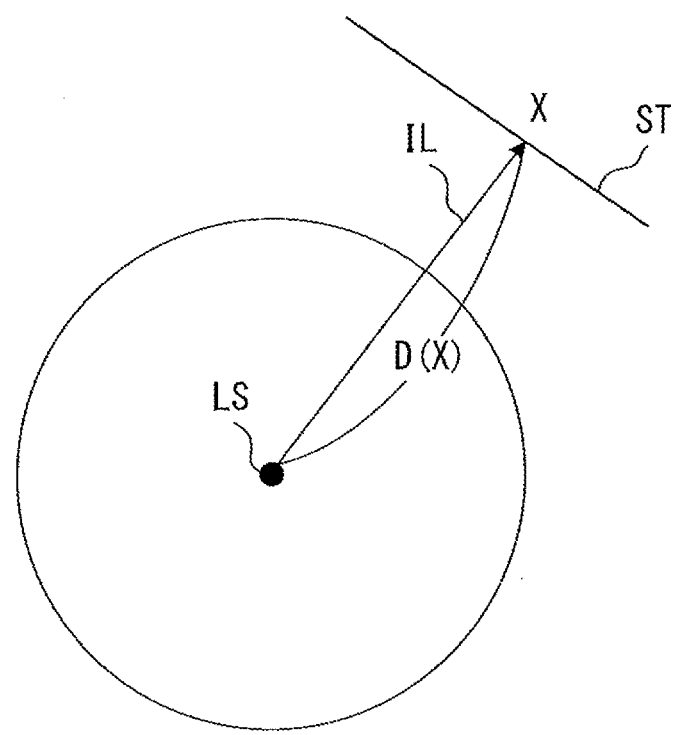
FIG. 2 is a diagram explaining a relationship between a luminance value and a distance in a case in which a light source is a point light source.

FIG. 2 is a diagram explaining a relationship between a luminance value I(X) and a distance D(X) in a case in which a light source LS is a point light source. The luminance value I(X) is a luminance value at a point X on a subject ST in a captured image, as described above. The point X is defined by an image coordinate system with the center of the captured image as an origin. The distance D(X) is a distance between a position on the subject ST that corresponds to the point X and the light source LS, as described above. In this case, because the light source LS is a point light source, the luminance value I(X) is proportional to $(1/D(X)^2)$.

Figure 3:
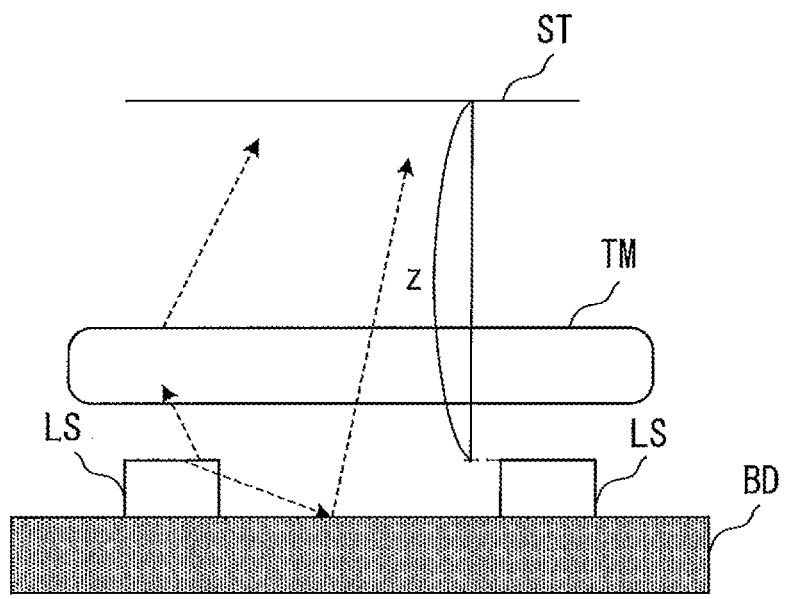
FIG. 3 is a diagram explaining a relationship between a luminance value and a distance in a biometric authentication device.

FIG. 3 is a diagram explaining a relationship between the luminance value I(X) and the distance D(X) in the biometric authentication device 100. An actual biometric authentication device 100 includes a plurality of light sources LS provided on a board BD, and a light guide TM, as illustrated in FIG. 3. The subject ST is illuminated with illumination light IL from the plurality of light sources LS in such a way that the light guide TM makes the distribution of the illumination intensity uniform. An arrow drawn with a broken line in FIG. 3 represents internal reflection generated by internal parts or the like. As described above, the actual biometric authentication device 100 includes the plurality of light sources LS, and is influenced by internal reflection. Namely, the actual biometric authentication device 100 has a great deviation from the point light source model, and therefore the luminance value I(X) is not always proportional to $(1/D(X)^2)$.

Accordingly, it is assumed in Embodiment 1 that the luminance value I(X) is proportional to $(1/D(X)^\alpha)$. Stated another way, it is assumed that the luminance value I(X) is calculated according to the following expression 2.

$$I(X) = I_0 \frac{\cos\theta i}{D(X)^\alpha} \quad (2)$$

In this expression, a coefficient α is a coefficient that represents distance dependency of the illumination intensity, and an appropriate value is set for the coefficient α in accordance with conditions of a sensor and the subject ST, as described later in detail.

Figure 4:
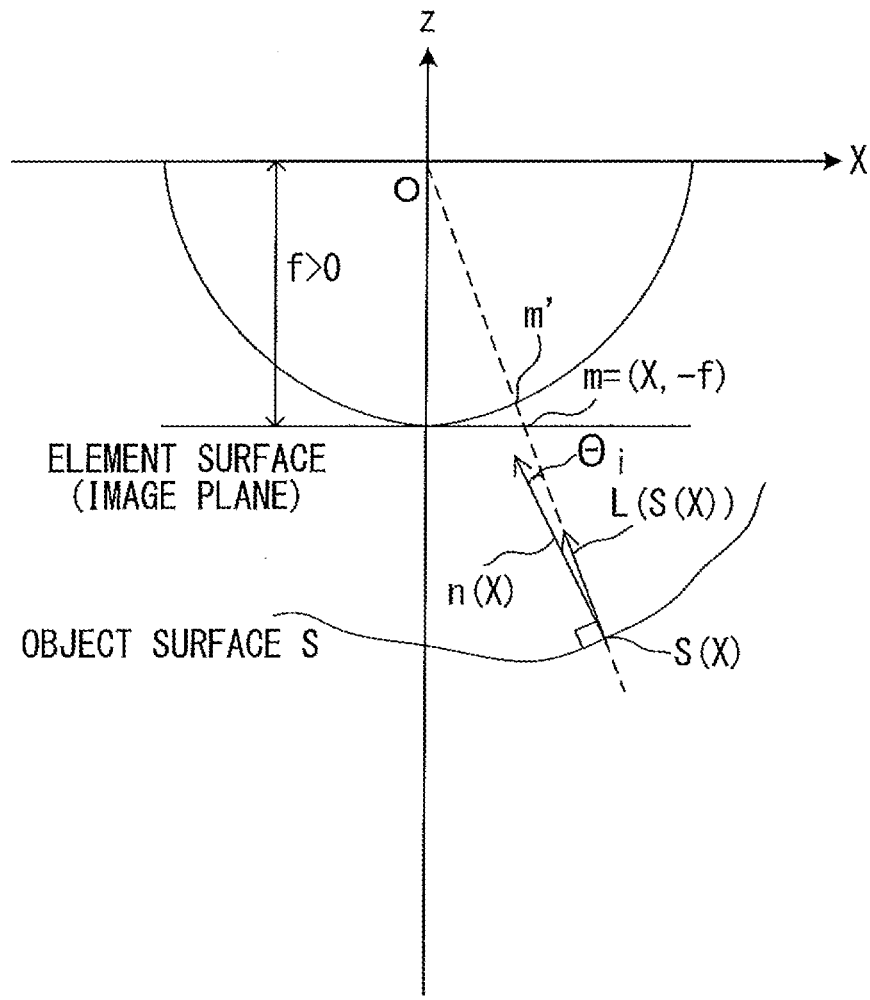
FIG. 4 illustrates an optical model used in Non-Patent Document 3.

With reference to FIG. 4, an outline of a process of calculating a three-dimensional shape of a subject ST described in Non-Patent Document 3 is described below. FIG. 4 illustrates an optical model used in Non-Patent Document 3. It is assumed that an imaging device is a pinhole camera model and that the subject ST has a complete diffusion reflection characteristic. It is also assumed that an illumination intensity decreases in inverse proportion to the square of a distance between a light source LS and the subject ST, and that the light source LS is located at the center of a lens (an origin O in FIG. 4).

An element surface (an image plane) in which an image sensor exists, that is, a luminance value at a point m in FIG. 4 is usually used, while in Non-Patent Document 3, a luminance value at a point m' on a circle having a radius f with the origin O as a center is used. The radius f is the shortest distance between the center of the lens (the origin O) and the element surface, namely, a focal distance, and the point m' is an intersection of a line connecting the origin O with the point m and the circle having the radius f as the origin O as a center.

When Q is a set of points on the image plane and S(X) is a point on an object surface of the subject ST that corresponds to the point X on the image plane, the object surface S of the subject ST can be expressed by the following expression 3. In this expression, X=(xi, yi) is established, and S(X) is an intersection of the line connecting the origin O with the point m and the object surface S of the subject ST.

$$S = \{S(X) : X \in \Omega\} \quad (3)$$

A distance |m| from the origin O to the point m on the element surface can be expressed by the following expression 4 because m=(X, -f) is established.

$$|m| = \sqrt{|X|^2 + f^2} \quad (4)$$

Accordingly, the point m' can be expressed by the following expression 5 by using expression 4.

$$m' = \frac{f}{\sqrt{|X|^2 + f^2}} m \quad (5)$$

Further, S(X) can be expressed by the following expression 6, by using u(X) that is a function that satisfies S(X)=u(X)m' and represents an object shape of the subject ST.

$$S(X) = u(X)m' = \frac{fu(X)}{\sqrt{|X|^2 + f^2}}(X, -f) \quad (6)$$

Next, a relationship between the luminance value I(X) at the point X of the captured image (the image plane) and the function u(X) representing the object shape is derived. The luminance I(X) can be expressed by the following expression under the assumption that the illumination intensity decreases in inverse proportion to the square of the distance between the light source LS and the subject ST. Here, it is assumed that the constant $I_0$ is not considered. $\theta i$ in expression 7 is an angle that is formed by a normal vector n(X) of the object surface S at S(X) and a unit vector L(S(X)) in a direction of the light source LS (the origin O), and D(X) in expression 7 is a distance from the light source LS (the origin O) to the point S(X) on the object surface S.

$$I(X) = \frac{\cos\theta_i}{D(X)^2} \quad (7)$$

Here, the normal vector n(X) of the object surface S at the point S(X) can be expressed by the following expression 8. In expression 8, $\nabla$ represents a differential operator, and "·" represents an inner product.

$$n(X) = \left( f\nabla u(X) - \frac{fu(X)}{|X|^2 + f^2} X, \nabla u(X) \cdot X + \frac{fu(X)}{|X|^2 + f^2} f \right) \quad (8)$$

Further, the unit vector L(S(X)) in a direction of the light source LS (the origin O) at the point S(X) can be expressed by the following expression 9 by using coordinates of the point m.

$$L(S(X)) = \frac{1}{\sqrt{|X|^2 + f^2}}(-X, f) \quad (9)$$

cos $\theta i$ can be obtained from an inner product of a unit normal vector n(X)/|n(X)| and the unit vector L(S(X)) at the point S(X), and therefore the following expression 10 is satisfied.

$$\cos\theta_i = L(S(X)) \cdot \frac{n(X)}{|n(X)|} \quad (10)$$

When absolute values of both sides in expression 6 are calculated, |S(X)|=D(X) is established, and therefore the following expression 11 can be derived.

$$D(X) = fu(X) \quad (11)$$

Here, the following expression 12 can be derived from expressions 7 to 10.

$$D(X)^2 I(X) = \cos\theta_i = L(S(X)) \cdot \frac{n(X)}{|n(X)|} \quad (12)$$

$$= \frac{1}{\sqrt{|X|^2 + f^2}}(-X, f) \cdot$$

$$\frac{\left( f\nabla u(X) - \frac{fu(X)}{|X|^2 + f^2} X, \nabla u(X) \cdot X + \frac{fu(X)}{|X|^2 + f^2} f \right)}{|n(X)|}$$

$$= \frac{1}{|n(X)|\sqrt{|X|^2 + f^2}} \left[ \frac{fu(X)}{|X|^2 + f^2} |X|^2 + \frac{fu(X)}{|X|^2 + f^2} f^2 \right]$$

$$= \frac{fu(X)}{|n(X)|\sqrt{|X|^2 + f^2}}$$

Namely, the luminance value I(X) can be expressed by the following expression 13, by using expression 11.

$$I(X) = \frac{fu(X)}{|n(X)|\sqrt{|X|^2 + f^2}} \times \frac{1}{D(X)} = \frac{u(X)}{|n(X)|\sqrt{\frac{|X|^2 + f^2}{f^2}}} \times \frac{1}{f^2 u(X)^2} \quad (13)$$

Here, Q(X) is defined by the following expression 14.

$$Q(X) = \sqrt{\frac{f^2}{|X|^2 + f^2}} \qquad (14)$$

When $|n(X)|^2$ is developed, the following expression 15 can be derived from the definition of Q(X) in expression 14.

$$|n(X)|^2 = f^2|\nabla u(X)|^2 + (\nabla u(X) \cdot X)^2 + \qquad (15)$$
$$\frac{f^2 u(X)^2}{(|X|^2 + f^2)^2}(|X|^2 + f^2)$$
$$= f^2|\nabla u(X)|^2 + (\nabla u(X) \cdot X)^2 + \frac{f^2}{(|X|^2 + f^2)}u(X)^2$$
$$= f^2|\nabla u(X)|^2 + (\nabla u(X) \cdot X)^2 + Q(X)^2 u(X)^2$$

The following expression 16 can be derived from expressions 13 to 15.

$$I(X) = \frac{u(X)}{\sqrt{[f^2|\nabla u(X)|^2 + (\nabla u(X) \cdot X)^2]/Q(X)^2 + u(X)^2}} \times \frac{1}{f^2 u(X)^2} \qquad (16)$$

By rearranging expression 16, the following expression 17 can be derived.

$$I(X)f^2 \frac{\sqrt{\frac{[f^2|\nabla u(X)|^2 + (\nabla u(X) \cdot X)^2]}{Q(X)^2} + u(X)^2}}{u(X)} - u(X)^{-2} = 0 \qquad (17)$$

When v(X) is defined by the following expression 18, $u(X)=e^{v(X)}$ is established, and $\nabla u(X)=e^{v(X)}\nabla v(X)$ is established. Note that e is a Napier's constant.

$$v(X)=\ln(u(X)) \qquad (18)$$

Accordingly, expression 17 can be expressed by the following expression 19.

$$-e^{-2v(X)}+J(X)\sqrt{f^2|p|^2+(p\cdot X)^2+Q(X)^2}=0 \qquad (19)$$

Note that p and J(X) in expression 19 are defined by expressions 20 and 21, respectively.

$$p = \nabla v(X) \qquad (20)$$

$$J(X) = \frac{I(X)f^2}{Q(X)} \qquad (21)$$

When expression 19 is solved for v(X), u(X) is obtained from expression 18, and the obtained u(X) is substituted in expression 6, the point S(X) on the object surface S can be calculated. Namely, the object surface S of the subject ST can be measured.

A process of calculating a three-dimensional shape of a subject ST in a model in which a distance-dependent coefficient of 2.0 employed in Embodiment 1 is generalized into a coefficient α (hereinafter referred to as a "distance-dependent variable model") is described next.

The luminance value I(X) can be expressed by the following expression 22 under the assumption that the illumination intensity decreases in inverse proportion to the a-th power of the distance between the light source LS and the subject ST. Here, it is assumed that the constant $I_0$ is not considered, similarly to the case described in Non-Patent Document 3.

$$I(X) = \frac{\cos\theta_i}{D(X)^\alpha} \qquad (22)$$

Similarly to the case described in Non-Patent Document 3, the following expression 23 can be derived from expressions 8 to 10 and expression 22.

$$D(X)^\alpha I(X) = \cos\theta_i \qquad (23)$$
$$= L(S(X)) \cdot \frac{n(X)}{|n(X)|}$$
$$= \frac{1}{|X|^2 + f^2}(-X, f) \cdot$$
$$\left(f\nabla u(X) - \frac{fu(X)}{|X|^2 + f^2}X, \nabla u(X) \cdot X + \frac{fu(X)}{|X|^2 + f^2}f\right) \Big/$$
$$|n(X)|$$
$$= \frac{1}{|n(X)|\sqrt{|X|^2 + f^2}}\left[\frac{fu(X)}{|X|^2 + f^2}|X|^2 + \frac{fu(X)}{|X|^2 + f^2}f^2\right]$$
$$= \frac{fu(X)}{|n(X)|\sqrt{|X|^2 + f^2}}$$

When both sides of expression 23 are divided by $(D(X)^\alpha)$ and expression 11 and the definition of Q(X) in expression 14 are applied, the following expression 24 can be derived from expression 23.

$$I(X) = \frac{fu(X)}{|n(X)|\sqrt{|X|^2 + f^2}} \times \frac{1}{D(X)^\alpha} \qquad (24)$$
$$= \frac{u(X)}{|n(X)|\sqrt{\frac{|X|^2 + f^2}{f^2}}} \times \frac{1}{f^\alpha u(X)^\alpha}$$
$$= \frac{u(X)}{|n(X)|/Q(X)} \times \frac{1}{f^\alpha u(X)^\alpha}$$

Further, by substituting expression 15, the following expression 25 can be derived from expression 24.

$$I(X) = \frac{u(X)}{\sqrt{[f^2|\nabla u(X)|^2 + (\nabla u(X) \cdot X)^2]/Q(X)^2 + u(X)^2}} \times \frac{1}{f^\alpha u(X)^\alpha} \qquad (25)$$

When expression 25 is rearranged, the following expression 26 can be derived.

$$I(X)f^\alpha \frac{\sqrt{[f^2|\nabla u(X)|^2 + (\nabla u(X) \cdot X)^2]/Q(X)^2 + u(X)^2}}{u(X)} - u(X)^{-\alpha} = 0 \qquad (26)$$

Here, in the distance-dependent variable model, v(X) is defined by the following expression 27. Namely, in Non-Patent Document 3, a natural logarithm is calculated, as expressed in expression 18, but in the distance-dependent variable model, a logarithm with a base of a constant b (b>0) is calculated.

$$v(X) = \log_b(u(X)) \tag{27}$$

In this case, u(X) and v(X) has a relationship expressed by the following expression 28.

$$u(X) = e^{\beta v(X)}$$

$$\nabla u(X) = \beta e^{\beta v(X)} \nabla v(X)$$

where $\beta = \ln(b)$ \hfill (28)

When expression 28 is applied to expression 26, the following expression 29 can be derived from expression 26.

$$I(X)f^\alpha \frac{\sqrt{[f^2|\nabla u(X)|^2 + (\nabla u(X) \cdot X)^2]/Q(X)^2 + u(X)^2}}{u(X)} - u(X)^{-\alpha} = \tag{29}$$

$$-e^{-\alpha\beta v(X)} + \left[\frac{I(X)f^\alpha}{Q(X)}\right]$$

$$\sqrt{[f^2\beta^2|\nabla v(X)|^2 + \beta^2(\nabla v(X) \cdot X)^2] + Q(X)^2} = -e^{-\alpha\beta v(X)} + \left[\frac{I(X)f^\alpha \beta}{Q(X)}\right]\sqrt{[f^2|\nabla v(X)|^2 + (\nabla v(X) \cdot X)^2] + \left(\frac{Q(X)^2}{\beta^2}\right)} = 0$$

Further, Q'(X), J'(X), and p are defined by the following expressions 30, 31, and 32, respectively.

$$Q'(X) = \frac{Q(X)}{\beta} = \frac{1}{\beta}\sqrt{\frac{f^2}{|X|^2 + f^2}} \tag{30}$$

$$J'(X) = \frac{I(X)f^\alpha}{Q'(X)} \tag{31}$$

$$p = \nabla v(X) \tag{32}$$

In this case, the following expression 33 can be derived from expression 29.

$$-e^{-\alpha\beta v(X)} + \left[\frac{I(X)f^\alpha \beta}{Q(X)}\right]\sqrt{[f^2|\nabla v(X)|^2 + (\nabla v(X) \cdot X)^2] + \left(\frac{Q(X)^2}{\beta^2}\right)} = \tag{33}$$

$$-e^{-\alpha\beta v(X)} + J'(X)\sqrt{f^2|p|^2 + (p \cdot X)^2 + Q'(X)^2} = 0$$

When expression 19 in Non-Patent Document 3 and expression 33 in the distance-dependent variable model are compared and β is set so as to satisfy αβ=2, expression 33 in the distance-dependent variable model can be expressed by the following expression 34.

$$-e^{-v(X)} + J'(X)\sqrt{f^2|p|^2 + (p \cdot X)^2 + Q'(X)^2} = 0 \tag{34}$$

In addition, Q'(X) can be expressed by the following expression 35.

$$Q'(X) = \frac{\alpha}{2}\sqrt{\frac{f^2}{|X|^2 + f^2}} \tag{35}$$

Further, the following expression 36 can be derived from the relationship between u(X) and v(X) expressed by expression 28.

$$u(X) = b^{v(X)} = e^{\frac{2}{\alpha}v(X)} \tag{36}$$

When natural logarithms of both sides of expression 36 are calculated, the following expression 37 can be derived.

$$v(X) = \frac{\alpha}{2}\ln(u(X)) \tag{37}$$

As a result of the above calculation, it is apparent that a differential equation of expression 34 in the distance-dependent variable model is the same as a differential equation of expression 19 in Non-Patent Document 3, except for coefficients v(X), Q'(X), and J'(X), and that the differential equation of expression 34 in the distance-dependent variable model completely coincides with the differential equation of expression 19 in Non-Patent Document 3 when α=2.0 is established. Namely, a calculation method examined in Non-Patent Document 3 can be applied to the distance-dependent variable model.

Figure 5:
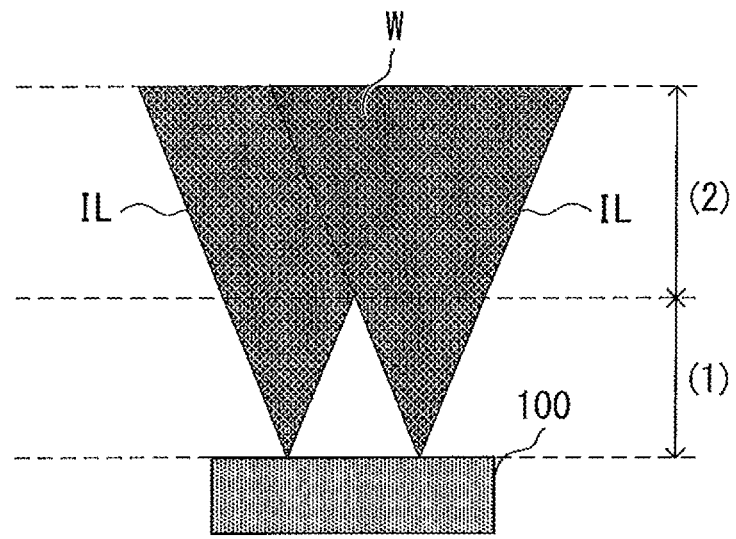
FIG. 5 is a diagram explaining a relationship between a height of a subject and a coefficient α according to Embodiment 1.

FIG. 5 is a diagram explaining a height z of a subject ST and a coefficient α according to Embodiment 1. W in FIG. 5 represents a portion in which rays of illumination light IL emitted from two light sources LS of the biometric authentication device 100 overlap each other. In a case in which the height z of the subject ST is within a height range (1), the illumination light IL illuminating the subject ST can be approximated to the illumination light IL from one of the light sources LS, as illustrated in FIG. 5. Namely, α≈2 is established.

In a case in which the height z of the subject ST is within a height range (2), the illumination light IL illuminating the subject ST is approximated to rays of the illumination light IL from the two light sources LS, as illustrated in FIG. 5. Namely, α<2 is established.

As described above, an appropriate value of the coefficient α varies according to the height z of the subject ST. Accordingly, in Embodiment 1, an accuracy in measuring a three-dimensional shape of the subject ST by using the SFS technique can be improved by changing the coefficient α according to an average height of the subject ST.

FIG. 6 is a functional block diagram illustrating an exemplary configuration of the biometric authentication device 100 according to Embodiment 1. The biometric authentication device 100 according to Embodiment 1 includes an imaging unit 10, a distance sensor 20, a storage 30, and a controller 40, as illustrated in FIG. 6.

The imaging unit 10 includes an image sensor such as a Complementary Metal Oxide Semiconductor (CMOS) image sensor, a lighting device such as a Light Emitting Diode (LED), and the like. The imaging unit 10 illuminates the subject (in Embodiment 1, a palm) ST under the control of the controller 40, and images the subject ST with the subject ST illuminated. The imaging unit 10 then stores a captured image in a data area of the storage 30 under the control of the controller 40.

The distance sensor 20 is sensor that measures the height z of the subject ST. The height z of the subject ST may be measured in a well-known method other than a method using the distance sensor 20. An example of such a method is a method proposed, for example, in Patent Document 1. The method proposed in Patent Document 1 is a method using a spot image for measuring a height. In the method, the subject ST is illuminated with illumination light IL narrowed in a beam shape, and a height z from a spot position to the subject ST is calculated.

The storage 30 includes, for example, a Random Access Memory (RAM), a Read Only Memory (ROM), a flash memory, and the like. The storage 30 functions as a work area of, for example, a Central Processing Unit (CPU) included in the controller 40, a program area in which various programs are stored such as an operation program for controlling the entirety of the biometric authentication device 100, and a data area in which various types of data are stored.

The storage 30 also functions as a coefficient storage 31 and a database 32, as illustrated in FIG. 6.

The coefficient storage 31 is a storage that stores information indicating a relationship between a height zr of a reference object RF and a coefficient $\alpha(zr)$. The reference object RF is a plane body for which a reflectance is constant and known.

Figure 8:
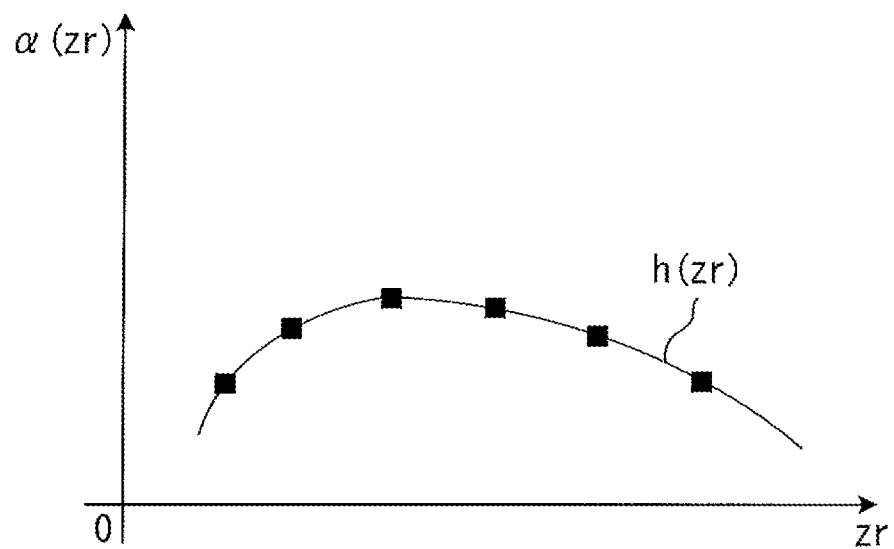
FIG. 8 illustrates another example of information that is stored in a coefficient storage according to Embodiment 1 and that indicates a relationship between a height of a reference object and a coefficient α.

FIGS. 7 and 8 illustrate examples of information that is stored in the coefficient storage 31 according to Embodiment 1 and that indicates a relationship between the height zr of the reference object RF and the coefficient $\alpha(zr)$. FIG. 7 illustrates an example in a case in which the information indicating the relationship between the height zr of the reference object RF and the coefficient $\alpha(zr)$ is a table in which a coefficient $\alpha(zrk)$ is associated with each of a height zrk (k=1, 2, 3, ...). FIG. 8 illustrates an example in a case in which the information indicating the relationship between the height zr of the reference object RF and the coefficient $\alpha(zr)$ is an approximate function h(zr) indicating the relationship between the height zr of the reference object RF and the coefficient $\alpha(zr)$.

A method for obtaining the relationship between the height zr of the reference object RF and the coefficient $\alpha(zr)$ is described next. The reference object RF is imaged at a plurality of different heights, and the coefficient $\alpha(zr)$ is calculated on the basis of a luminance value Ir(X) at each of the plurality of different heights. It is assumed that the luminance value Ir(X) of a captured image of the reference object RF is inversely proportional to the $\alpha$-th power of a distance D(X), and that the reference object RF is not tilted, namely, that an angle formed by a sight line vector and a normal vector of the reference object RF is 0 degrees (cos 0=1). It is also assumed that the distance D(X) at a point X on the reference object RF is equal to the height zr. In this case, when logarithms of both sides of expression 2 are calculated, a linear relationship expressed by the following expression 38 can be obtained.

$$\log(I(X))=\log(I_0)-\alpha \log(zr) \qquad (38)$$

A minute height $\Delta z$ is set. Luminance values Ir(X) at the point X on captured images obtained when the reference object RF is imaged at three different heights zr1 (=zr), zr2 (=zr-$\Delta z$), zr3 (=zr+$\Delta z$) are assumed to be Ir, $z_1$ (X), Ir, $z_2$ (X), and Ir, $z_3$(X), respectively. In this case, three expressions relating to the coefficient $\alpha$ as expressed by the following expression 39 can be derived from expression 38.

$$\log(Ir,z_1(X))=\log(I_0)-\alpha \log(zr1)$$

$$\log(Ir,z_2(X))=\log(I_0)-\alpha \log(zr2)$$

$$\log(Ir,z_3(X))=\log(I_0)-\alpha \log(zr3) \qquad (39)$$

A coefficient $\alpha(zr)$ that generates the smallest error for the three expressions in expression 39 can be obtained, for example, in the least squares method.

Return now to FIG. 6. The database 32 stores data needed for biometric authentication. As an example, the database 32 stores feature data of an image for registration used for collation. The feature data of the image for registration is feature data that is extracted from an image captured when registering biological data of a user by a feature extracting unit 42 (described later in detail).

The controller 40 includes, for example, a CPU and the like, and executes an operation program stored in the program area of the storage 30 so as to realize functions of a three-dimensional shape measurement processing unit 41, a feature extracting unit 42, and a collation processing unit 43. The controller 40 also executes the operation program so as to perform processes such as a control process for controlling the entirety of the biometric authentication device 100 or an authentication process described later in detail.

The three-dimensional shape measurement processing unit 41 is described later in detail. Functions of the feature extracting unit 42 and the collation processing unit 43 are described first.

The feature extracting unit 42 extracts feature data from a captured image in a well-known method. More specifically, in registering biological data, the feature extracting unit 42 extracts feature data from a captured image stored in the data area of the storage 30, and registers the extracted feature data in the database 32.

In performing collation, the feature extracting unit 42 extracts feature data from a captured image in which a posture of the subject ST has been corrected by a posture correcting unit 41F described later in detail, and outputs the extracted feature data to the collation processing unit 43.

The collation processing unit 43 collates feature data for collation that has been input from the feature extracting unit 42 with feature data for registration that has been registered in the database 32, and stores a collation result in the data area of the storage 30. The collation result is, for example, a similarity ratio between the feature data for collation and the feature data for registration.

Figure 9:
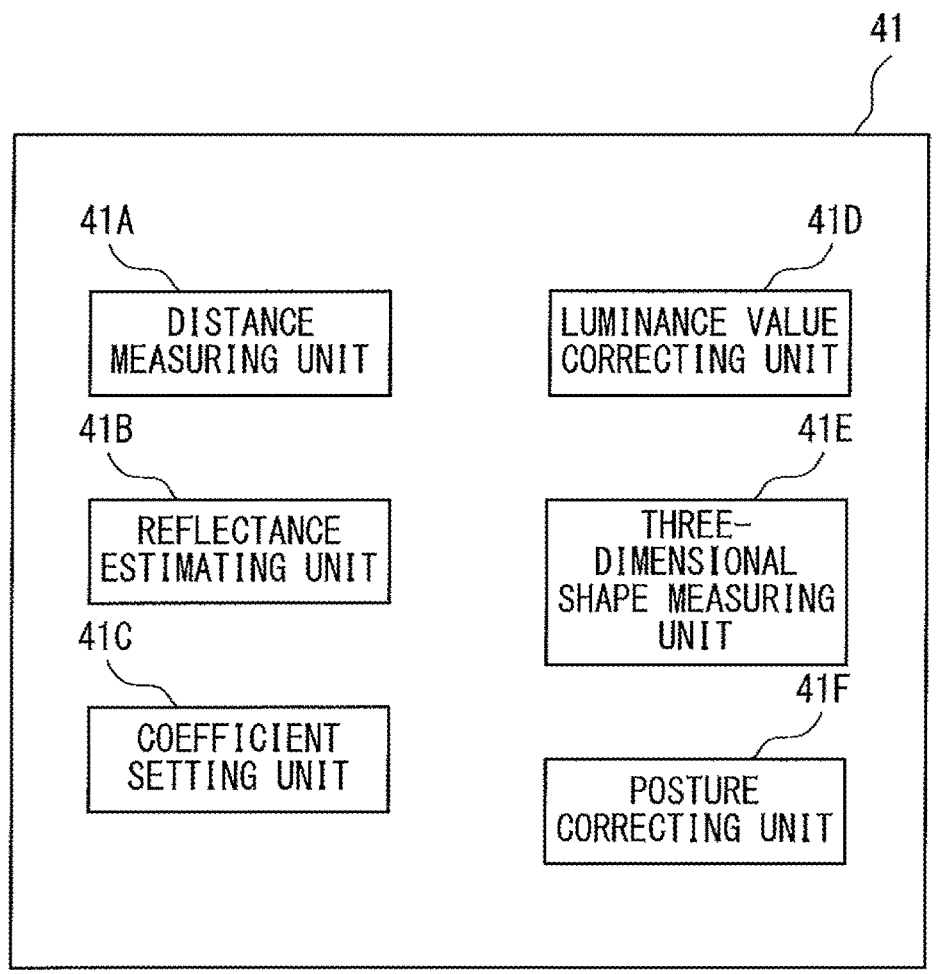
FIG. 9 is a functional block diagram illustrating an exemplary configuration of a three-dimensional shape measurement processing unit according to Embodiment 1.

FIG. 9 is a functional block diagram illustrating an exemplary configuration of the three-dimensional shape measurement processing unit 41 according to Embodiment 1. The three-dimensional shape measurement processing unit 41 measures a three-dimensional shape of the subject ST, and performs a process of correcting a posture (angle) of the subject ST in a captured image in accordance with a measurement result. The three-dimensional shape measurement processing unit 41 functions as a distance measuring unit 41A, a reflectance estimating unit 41B, a coefficient setting unit 41C, a luminance value correcting unit 41D, a three-dimensional shape measuring unit 41E, and a posture correcting unit 41F, as illustrated in FIG. 9.

The distance measuring unit 41A controls the distance sensor 20 so as to detect a height z from the light source LS to the subject ST. If the distance sensor 20 can detect heights z in a plurality of positions on the subject ST, an average of the heights z is obtained, and the obtained average height is determined to be a height of the subject ST.

The reflectance estimating unit 41B estimates a reflectance $R_f$ of the subject ST, and performs correction to cancel the reflectance $R_f$ peculiar to the subject ST. The reflectance $R_f$ of the subject ST varies according to users, for example, when the subject ST is a palm ST. Therefore, the reflectance $R_f$ of the subject ST is estimated, and correction to cancel the reflectance $R_f$ peculiar to the subject ST is performed on a luminance value Is(X) of a captured image. By doing this, the subject ST can be regarded as an object having the same reflectance as that of the reference object RF. Accordingly, a three-dimensional shape of the subject ST can be stably measured by using the SFS technique, regardless of the type of the subject ST.

The reflectance estimating unit 41B first obtains the luminance value Is(X) of a captured image at a point X that corresponds to a position on the subject ST in which the height z of the subject ST is detected by the distance sensor 20. The reflectance estimating unit 41B then obtains a luminance value Ir,z(X) at a point X of the reference object RF at the same height as the height z of the subject ST.

Then, the reflectance estimating unit 41B estimates the reflectance $R_f$ of the subject ST in a case in which the reflectance of the reference object RF is assumed to be "1.0", in accordance with the following expression 40.

$$R_f = \frac{Is(X)}{Ir, z(X)} \quad (40)$$

The reflectance estimating unit 41B performs correction to cancel the reflectance $R_f$ peculiar to the subject ST in accordance with the following expression 41, and outputs the corrected luminance value Is' (X) to the luminance value correction unit 41D.

$$Is'(X)=Is(X)/R_f \quad (41)$$

The luminance value Ir,z(X) can be obtained by storing captured images of the reference object RF that have been captured, for example, at prescribed height intervals in the data area of the storage 30. When a captured image of the reference object RF at the same height as the height z of the subject ST is not stored in the data area of the storage 30, the reflectance estimating unit 41B can estimate the luminance value Ir,z(X) at the point X of the reference object RF at the same height as the height z of the subject ST, for example, with linear interpolation.

As another example, the luminance value Ir,z(X) can be obtained (calculated) by storing a coefficient of a function for calculating the luminance value Ir,z(X) in the data area of the storage 30. A function indicating an approximate curve can be obtained by performing curve approximation on the basis of luminance values of captured images of the reference object RF, for example, at three different heights z1, z2, and z3. The function indicating the approximate curve can be expressed, for example, by the following expression 42.

$$Ir,z(X)=[A(X)/Dr,z(X)^2]+[B(X)/Dr,z(X)]+C(X) \quad (42)$$

Dr,z(X) in expression 42 is a distance from the light source LS to a position that corresponds to the point X of the reference object RF in a case in which the reference object RF is located at the height z. A(X), B(X), and C(X) in expression 42 are coefficients of a function indicating an approximate curve for the point X of the reference object RF. In the case of an ideal point light source, only the term $(Dr, z(X)^{-2})$ in the above expression 42 is valid, but in the actual biometric authentication device 100, a light source greatly deviates from the ideal point light source, and therefore the function indicating the approximate curve fails to be expressed by using only the term $(Dr, z(X)^{-2})$. Accordingly, a function including the coefficients B(X) and C(X) is assumed to be a function indicating the approximate curve.

When an imaging device of the biometric authentication device 100 according to Embodiment 1 is assumed to be a pinhole camera model, a position (x,y,z) in a three-dimensional coordinate system that corresponds to the point X=(xi,yi) on a captured image can be expressed by the following expression 43 in a case in which the height z is known. In expression 43, f is a focal distance.

$$x=(z/f)xi$$

$$y=(z/f)yi \quad (43)$$

Namely, coordinates (x,y,z) on the reference object RF that correspond to the point X on the captured image can be obtained. Accordingly, a distance Dr,z(X) from the light source LS to the coordinates (x,y,z) that correspond to the point X of the reference object RF can be calculated according to the following expression 44.

$$Dr,z(X)=\sqrt{x^2+y^2+z^2} \quad (44)$$

A method for calculating coefficients A(X), B(X), and C(X) at the point X on the captured image is described next. Luminance values Ir, $z_1$(X), Ir, $z_2$(X), and Ir, $z_3$(X) at the point X of the reference object RF at three different heights z1, z2, and z3 can be calculated according to the following expression 45 on the basis of expression 42.

$$Ir,z_1(X)=[A(X)/Dr,z_1(X)^2]+[B(X)/Dr,z_1(X)]+C(X)$$

$$Ir,z_2(X)=[A(X)/Dr,z_2(X)^2]+[B(X)/Dr,z_2(X)]+C(X)$$

$$Ir,z_3(X)=[A(X)/Dr,z_3(X)^2]+[B(X)/Dr,z_3(X)]+C(X) \quad (45)$$

The distances $Dr,z_1(X)$, $Dr,z_2(X)$, and $Dr,z_3(X)$ in expression 45 can be calculated from expressions 43 and 44 by applying the height of the reference object RF when the point X on the captured image and the focal distance f are determined. Accordingly, expression 45 includes three simultaneous equations that correspond to three unknown coefficients A(X), B(X), and C(X). Therefore, the coefficients A(X), B(X), and C(X) can be obtained by solving these simultaneous equations.

By storing a set of the coefficients A(X), B(X), and C(X) obtained as described above in the data area of the storage 30 in association with the point X (pixel X), the reflectance estimating unit 41B can obtain (calculate) the luminance value Ir,z(X) at the point X (pixel X) of the reference object RF at the same height as the height z of the subject ST. FIG. 10 illustrates an example of information in which a set of coefficients (A(X), B(X), and C(X)) is associated with each of the pixels stored in the storage 30 according to Embodiment 1.

Return now to FIG. 9. The coefficient setting unit 41C sets a coefficient α that is used to perform a process of correcting a luminance value and to measure a three-dimensional shape of the subject ST by using the SFS technique according to various conditions such as the height z of the subject ST, the size of a sensor, and the like. In Embodiment 1, the coefficient setting unit 41C sets the coefficient α according to the height z of the subject ST.

More specifically, the coefficient setting unit 41C specifies a coefficient α that corresponds to the height z of the subject ST measured by the distance measuring unit 41A on the basis of the information that has been stored in the coefficient storage 31 and that indicates the relationship between the height zr and the coefficient α(zr), and sets the specified coefficient α. When the information that has been stored in the coefficient storage 31 and that indicates the relationship between the height zr and the coefficient α(zr) is a table as illustrated in FIG. 7, and a coefficient α(zr) that coincides with the height z of the subject ST has not been registered in the table, the coefficient setting unit 41C estimates the coefficient α of the height z of the subject ST, for example, with linear interpolation, and sets the estimated coefficient α.

The luminance value correcting unit 41D further corrects the luminance value Is'(X) input by the reflectance estimating unit 41B, by using the luminance value Ir,z(X) of the reference object RF, in order to reduce influence of peripheral darkening.

More specifically, the luminance value correcting unit 41D obtains (calculates) the luminance value Ir,z(X) at the point X of the reference object RF at the height z of the subject ST in the method above. Then, the luminance value correcting unit 41D calculates a correction coefficient δ(X) for each of the points X on the captured image in accordance with the following expression 46. In expression 46, P is a constant, and the coefficient α is the coefficient α set by the coefficient setting unit 41C.

$$\delta(X) = \left[\frac{P}{Ir, z(X)Dr, z(X)^\alpha}\right] \quad (46)$$

Then, the luminance value correcting unit 41D further corrects the luminance value Is'(X) in accordance with the following expression 47, and outputs the corrected Is"(X) to the three-dimensional shape measuring unit 41E.

$$Is''(x) = Is'(X)\delta(X) \quad (47)$$

When a coefficient k(X) is assumed to be defined by the following expression 48, the coefficient k(X) represents peripheral darkening in a cases in which the luminance value Ir, z(X) at the point X of the reference object RF is proportional to $(1/Dr, z(X)^\alpha)$. Accordingly, influence of peripheral darkening can be cancelled by employing the reciprocal of peripheral darkening for the correction coefficient δ(X). As described above, an accuracy in measuring the three-dimensional shape of the subject ST can be improved by removing a factor that is not considered in the conventional SFS technique, such as peripheral darkening.

$$k(X) = Ir, z(X)Dr, z(X)^\alpha \quad (48)$$

The three-dimensional shape measuring unit 41E calculates a differential equation of the distance-dependent variable model above by using the luminance value Is"(X) input by the luminance value correcting unit 41D and the coefficient α set by the coefficient setting unit 41C so as to measure the three-dimensional shape of the subject ST (a distance from the light source LS to a position of a three-dimensional coordinate system that corresponds to the point X on the captured image).

The posture correcting unit 41F corrects a posture of the subject ST in the captured image on the basis of the three-dimensional shape of the subject ST measured by the three-dimensional shape measuring unit 41E. More specifically, the posture correction unit 41F calculates an angle of a tilt of the subject ST to a reference plane on the basis of the three-dimensional shape of the subject ST measured by the three-dimensional shape measuring unit 41E. The reference plane is a plane parallel to a horizontal line drawn with a broken line in FIG. 1, as an example.

The angle of the tile of the subject ST to the reference plane can be obtained, for example, by projecting the three-dimensional shape of the subject ST measured by the three-dimensional shape measuring unit 41E to two dimensions and performing linear approximation on a two-dimensional projection. In this case, a tilt of the subject ST to an XZ plane by projecting the three-dimensional shape of the subject ST onto the XZ plane and performing linear approximation on a projection on the XZ plane. Similarly, a tilt of the subject ST to a YZ plane by projecting the three-dimensional shape of the subject ST onto the YZ plane and performing linear approximation on a projection on the YZ plane. An angle of a tilt of the subject ST to the reference plane can be obtained by obtaining the tilts of the subject ST to the XZ plane and the YZ plane. The angle of the tilt of the subject ST to the reference plane may be obtained by directly applying a plane equation to the three-dimensional shape of the subject ST.

The posture correcting unit 41F corrects the posture of the subject ST in the captured image in such a way that the angle of the tilt of the subject ST to the reference plane is "0", namely in such a way that the subject ST is parallel to the reference plane. The posture correcting unit 41F then outputs the corrected captured image to the feature extracting unit 42.

Figure 11:
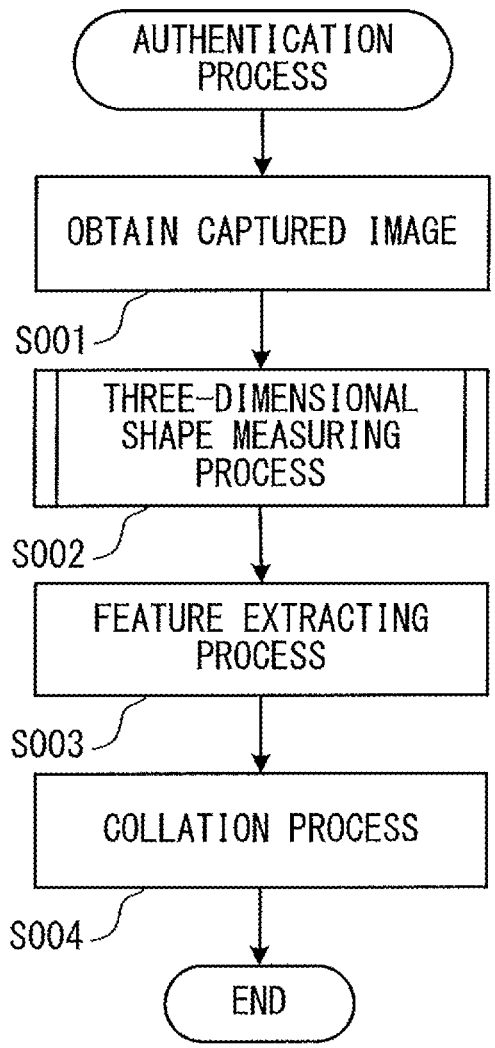
FIG. 11 is an exemplary flowchart explaining a flow of an authentication process according to Embodiment 1.

With reference to FIG. 11, a flow of an authentication process according to Embodiment 1 is described next. FIG. 11 is an exemplary flowchart explaining the flow of the authentication process according to Embodiment 1.

The controller 40 controls the imaging unit 10 to image the subject ST with the subject ST illustrated so as to obtain a capture image, and stores the obtained captured image in the data area of the storage 30 (step S001). The three-dimensional shape measurement processing unit 41 performs a three-dimensional shape measuring process so as to measure a three-dimensional shape of the subject ST, and corrects a posture of the subject ST in the captured image (step S002).

The feature extracting unit 42 extracts feature data from the captured image in which the posture of the subject ST has been corrected (step S003). The collation processing unit 43 collates the feature data extracted in step S003 with feature data for registration that is stored in the database 32, and stores a collation result in the data area of the storage 30 (step S004). Then, the process is finished.

Figure 12:
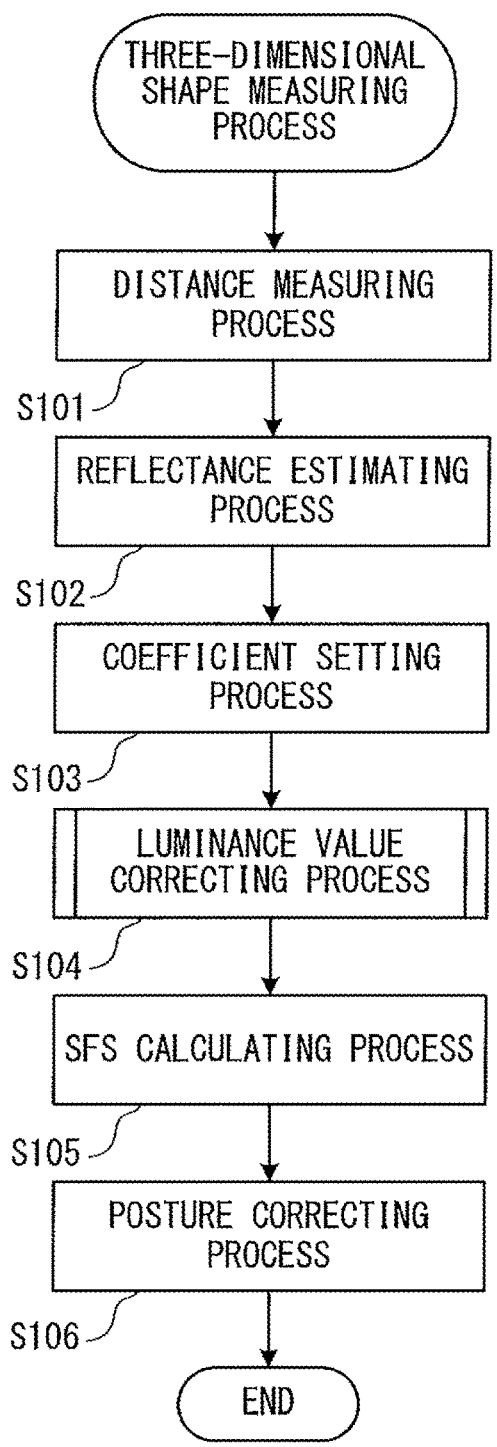
FIG. 12 is an exemplary flowchart explaining a flow of a three-dimensional shape measuring process according to Embodiment 1.

With reference to FIG. 12, a flow of a three-dimensional shape measuring process according to Embodiment 1 is described next. FIG. 12 is an exemplary flowchart explaining the flow of the three-dimensional shape measuring process according to Embodiment 1. The three-dimensional shape measuring process is a process that corresponds to the process of step S002 in the authentication process.

The distance measuring unit 41A controls the distance sensor 20 to detect the height z of the subject ST (step S101). The reflectance estimating unit 41B estimates a reflectance $R_f$ of the subject ST according to expression 40 described above, and performs correction to cancel the reflectance $R_f$ peculiar to the subject ST from the luminance value Is (X) at the point X of the captured image according to expression 41 described above (step S102).

The coefficient setting unit 41C sets a coefficient α that corresponds to the height z of the subject ST (step S103). The luminance value correcting unit 41D performs a luminance value correcting process so as to perform correction to cancel influence of peripheral darkening (step S104).

The three-dimensional shape measuring unit 41E calculates a differential equation of the distance-dependent variable model by using the luminance value Is" (X) after correction performed by the luminance value correcting unit 41D and the coefficient α so as to measure the three-dimensional shape of the subject ST (step S105). The posture correcting unit 41F corrects the posture of the subject ST in the captured image in such a way that the posture of the subject ST is parallel to the reference plane, on the basis of the three-dimensional shape of the subject ST (step S106). Then, this process is finished, and the process moves on to the process of step S003 in the authentication process.

Figure 13:
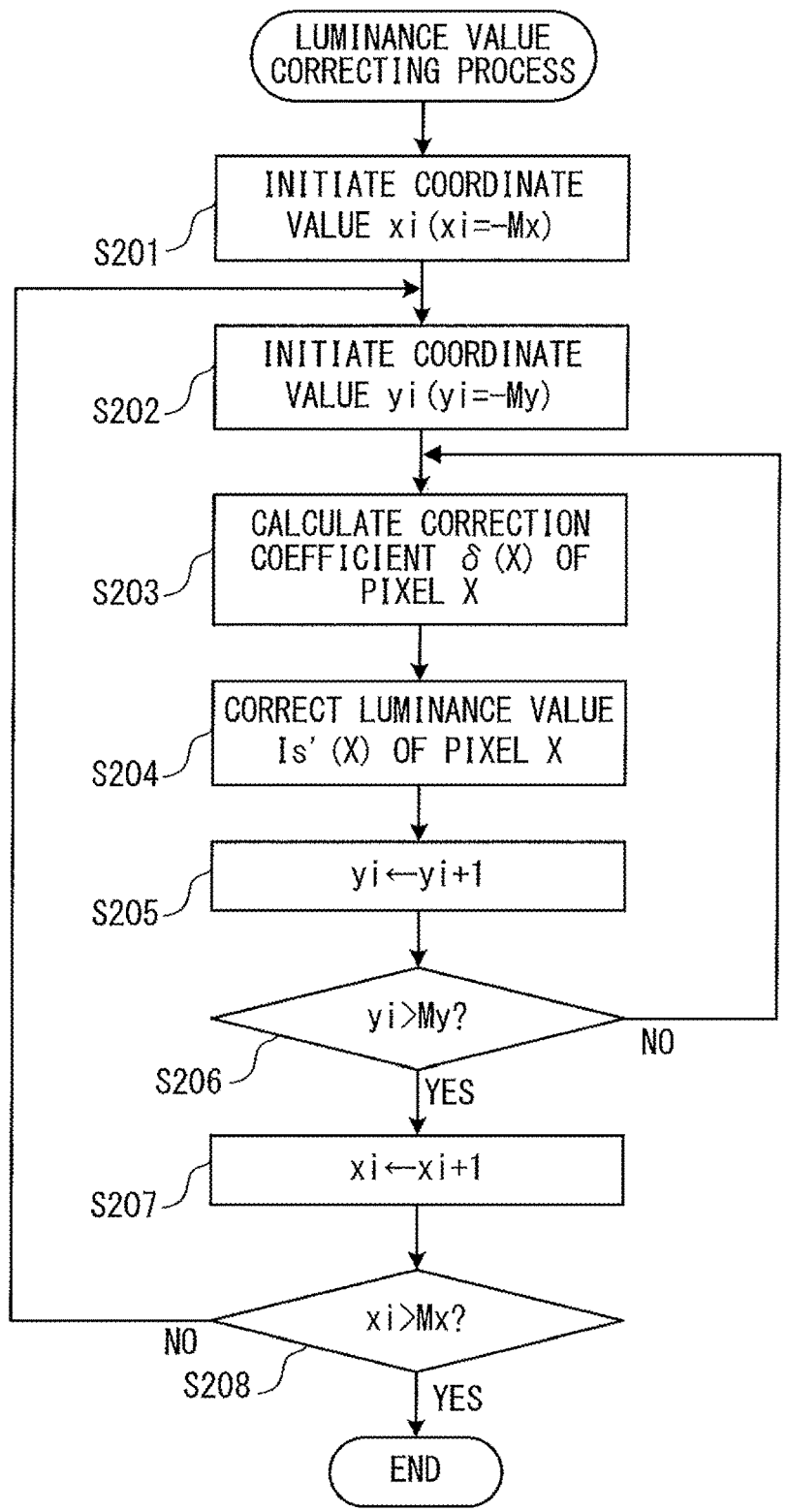
FIG. 13 is an exemplary flowchart explaining a flow of a luminance value correcting process according to Embodiment 1.

With reference to FIG. 13, a flow of a luminance value correcting process according to Embodiment 1 is described next. FIG. 13 is an exemplary flowchart explaining the flow of the luminance value correcting process according to Embodiment 1. The luminance value correcting process is a process that corresponds to the process of step S104 in the three-dimensional shape measuring process. The number of pixels of a captured image is assumed to be (2Mx+1)× (2My+1).

The luminance value correcting unit 41D initiates a coordinate value xi of a pixel X (step S201), and also initiates a coordinate value yi of the pixel X (step S202). Namely, the luminance value correcting unit 41D performs initiation so as to be xi=−Mx, and yi=−My.

The luminance value correcting unit 41D calculates a correction coefficient δ(X) of the pixel X according to expression 46 (step S203), and corrects the luminance value Is'(X) of the pixel X (step S204).

The luminance value correcting unit 41D increments the coordinate value yi of the pixel X (step S205), and determines whether the incremented coordinate value yi is greater than My (step S206). When the luminance value correcting unit 41D determines that the incremented coordinate value yi is less than or equal to My (step S206: NO), the process returns to the process of step S203, and the processes described above are repeated.

When the luminance value correcting unit 41D determines that the incremented coordinate value yi is greater than My (step S206: YES), the luminance value correcting unit 41D increments the coordinate value xi of the pixel X (step S207). The luminance value correcting unit 41D then determines whether the incremented coordinate value xi is greater than Mx (step S208).

When the luminance value correcting unit 41D determines that the incremented coordinate value xi is less than or equal to Mx (step S208: NO), the process returns to the process of step S202, and the processes described above are repeated. When the luminance value correcting unit 41D determines that the incremented coordinate value xi is greater than Mx (step S208: YES), this process is finished, and the process moves on to the process of step S105 in the three-dimensional shape measuring process.

According to Embodiment 1, the biometric authentication device 100 sets the coefficient α according to the height z of the subject ST. By doing this, an accuracy in measuring the three-dimensional shape of the subject ST measured by using the SFS technique can be improved, even when a relationship between a luminance value and a distance deviates from an ideal point light source model in which the luminance value is inversely proportional to the square of the distance, due to the height z of the subject ST.

In addition, according to Embodiment 1, the biometric authentication device 100 estimates the reflectance $R_f$ of the subject ST on the basis of the luminance value of the reference object RF and the luminance value of the captured image, and corrects the luminance value of the captured image in such a way that the reflectance of the subject ST is almost equal to the reflectance of the reference object RF. By doing this, the subject ST can be regarded as an object having the same reflectance as that of the reference object RF, and therefore the three-dimensional shape of the subject ST can be stably measured by using the SFS technique, regardless of the type of the subject ST.

Further, according to Embodiment 1, the biometric authentication device 100 performs, on the luminance value of the captured image, correction to remove influence of peripheral darkening on the luminance value of the captured image. An accuracy in measuring the three-dimensional shape of the subject ST can be improved by removing a factor that is not considered in the conventional SFS technique, such as peripheral darkening.

Furthermore, according to Embodiment 1, the biometric authentication device 100 corrects a tilt of the subject ST in a captured image on the basis of a measured three-dimensional shape of the subject ST. By doing this, a posture of the subject ST in the captured image can be corrected to the same posture as the posture in a captured image from which feature data for registration has been extracted, and therefore an authentication accuracy can be improved.

Embodiment 2

In Embodiment 1, a scheme for setting the coefficient α according the height z of the subject ST has been described. In Embodiment 2, a case is assumed in which a guiding member that guides a position of the subject ST is provided in a biometric authentication device 100. When the guiding member is provided in the biometric authentication device 100, the height z of the subject ST is fixed, but a position of the subject ST in the xy direction varies within a prescribed range, and is not fixed. Accordingly, in Embodiment 2, a scheme for setting the coefficient α according to the position of the subject ST in the xy direction in a case in which the height z of the subject ST is fixed is described. The coefficient α is set according to the position of the subject ST in the xy direction as described above because, in a case in which the biometric authentication device 100 includes a plurality of light sources LS, the number of light sources LS that illuminate the subject ST may vary depending on the position of the subject ST in the xy direction.

FIGS. 14A and 14B are diagrams explaining a relationship between a position of the subject ST on a horizontal plane (the position of the subject ST in the xy direction) and a coefficient α according to Embodiment 2. In the example illustrated in FIG. 14A, illumination light IL that illuminates the subject ST having a height z can be approximated to illumination light IL from one light source LS. Namely, α≈2 is estimated.

In the example illustrated in FIG. 14B, the subject ST is located in a portion in which rays of illumination light IL are overlapping each other, and therefore illumination light IL that illuminates the subject ST can be approximated to rays of illumination light IL from two light sources LS. Namely, α<2 is established.

Figure 15:
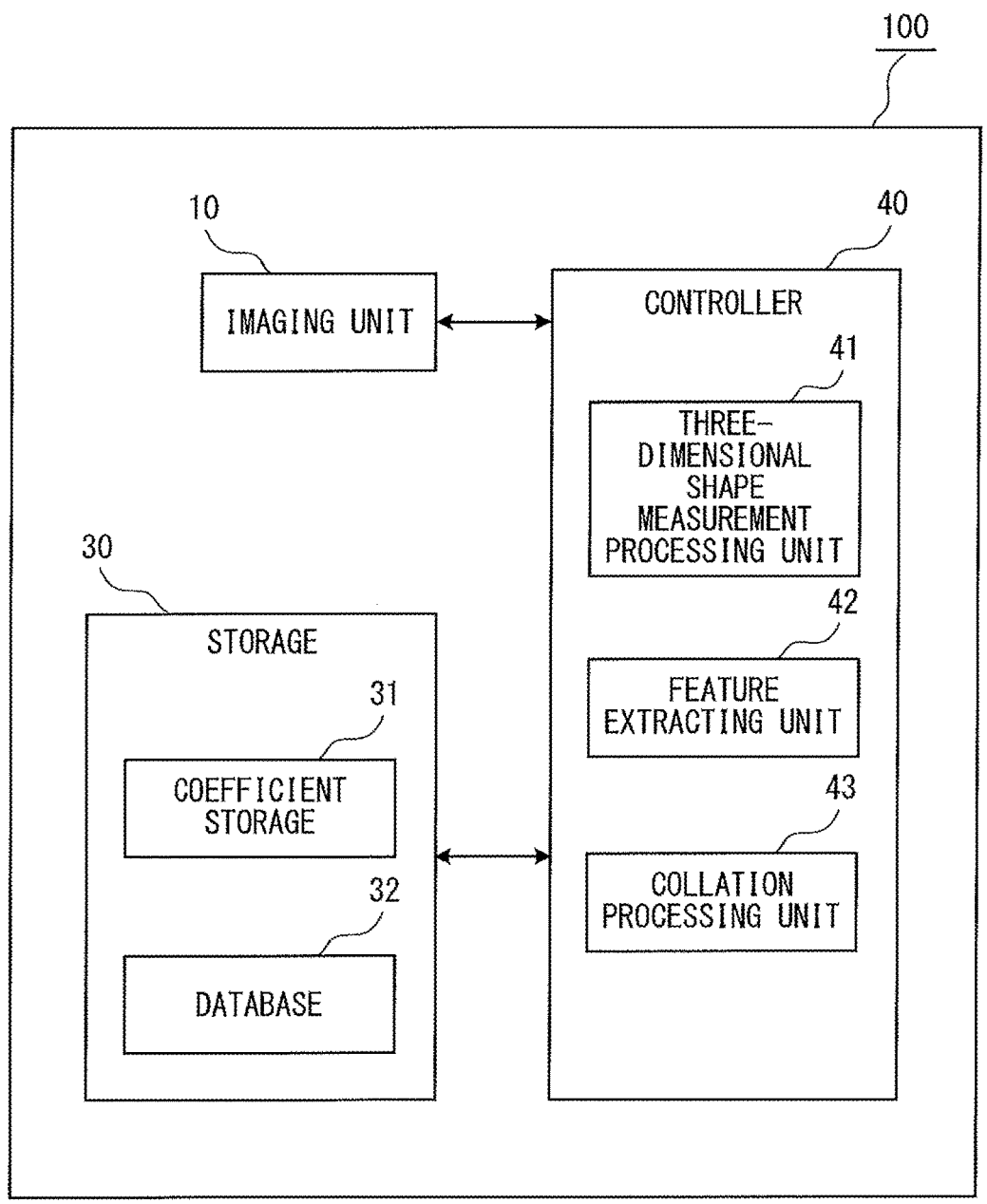
FIG. 15 is a functional block diagram illustrating an exemplary configuration of a biometric authentication device according to Embodiment 2.
Figure 16:
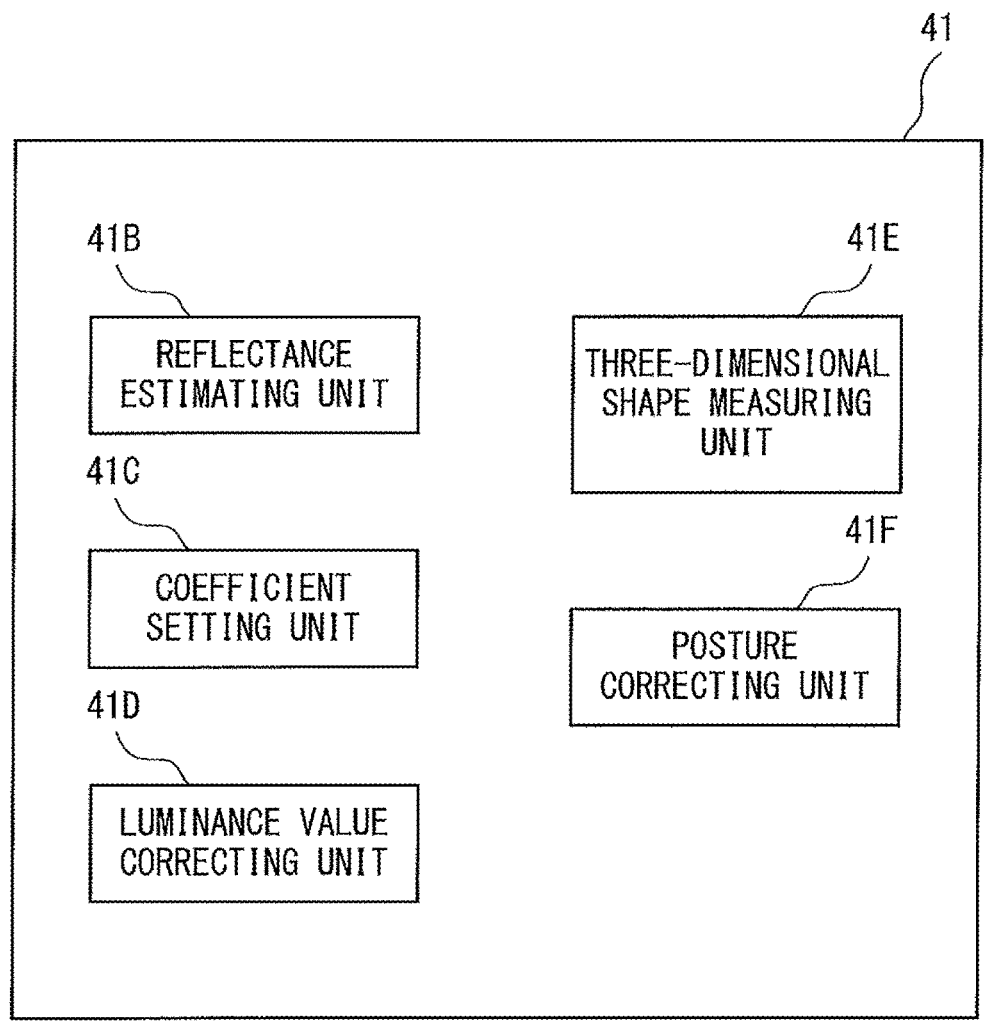
FIG. 16 is a functional block diagram illustrating an exemplary configuration of a three-dimensional shape measurement processing unit according to Embodiment 2.

FIG. 15 is a functional block diagram illustrating an exemplary configuration of a biometric authentication device 100 according to Embodiment 2. FIG. 16 is a functional block diagram illustrating an exemplary configuration of a three-dimensional shape measurement processing unit 41 according to Embodiment 2. A basic configuration of the biometric authentication device 100 according to Embodiment 2 is the same as the configuration according to Embodiment 1. However, the configuration according to Embodiment 2 is different from that according to Embodiment 1 in that the distance sensor 20 is not included, as illustrated in FIG. 15. The configuration according to Embodiment 2 is also different from that according to Embodiment 1 in that the three-dimensional shape measurement processing unit 41 does not include the distance measuring unit 41A, as illustrated in FIG. 16. In addition, there are slight differences between the configuration according to Embodiment 2 and the configuration according to Embodiment 1 in functions of the coefficient storage 31 and the coefficient setting unit 41C. Information relating to the height z of the subject ST fixed by the guiding member is assumed to be stored in the data area of the storage 30.

The coefficient storage 31 stores a function $F_\alpha(X)$ for calculating a coefficient $\alpha$ that corresponds to a point X (pixel X) in a captured image. Stated another way, the function $F_\alpha(X)$ is a function for calculating a coefficient $\alpha$ that corresponds to each of the points X on the subject ST included in the captured image. The coefficient storage 31 may store information in which the coefficient $\alpha$ is associated with each of the pixels, as illustrated in FIG. 17, instead of the function $F_\alpha(X)$. FIG. 17 illustrates an example of information that is stored in the coefficient storage 31 according to Embodiment 2 and in which the coefficient $\alpha$ is associated with each of the pixels.

The coefficient setting unit 41C sets the coefficient $\alpha$ according to a position of the subject ST in the xy direction in Embodiment 2. Namely, the coefficient setting unit 41C sets the coefficient $\alpha$ according to a position of the subject ST in a captured image. More specifically, the coefficient setting unit 41C specifies a region T in which the subject ST is located in the captured image in a well-known method, and calculates a mean value $\alpha_{AVE}$ of the coefficient $\alpha$ that corresponds to each of the pixels in the region T according to the following expression 49. In expression 49, $N_T$ is the number of pixels in the region T in which the subject ST is located. Expression 49 is an example in a case in which the coefficient storage 31 stores the function $F_\alpha(X)$.

$$\alpha_{AVE} = \sum_{X \in T} F_\alpha(X)/N_T \qquad (49)$$

The coefficient setting unit 41C sets the calculated mean value $\alpha_{AVE}$ to be the coefficient $\alpha$ used to perform the luminance value correcting process and to measure the three-dimensional shape of the subject ST by using the SFS technique.

By calculating the mean value $\alpha_{AVE}$ of the coefficient $\alpha$ in the region T in which the subject ST is located and measuring the three-dimensional shape of the subject ST on the basis of the calculated mean value $\alpha_{AVE}$, as described above, an accuracy in measuring the three-dimensional shape of the subject ST can be improved. This is because a single coefficient $\alpha$ needs to be used to measure the three-dimensional shape of the subject ST by using the SFS technique, although an optimum coefficient $\alpha$ differs for each of the points X on the captured image.

According to Embodiment 2, the biometric authentication device 100 sets the coefficient $\alpha$ on the basis of the position of the subject ST in the xy direction. By doing this, even when a relationship between a luminance value and a distance deviates from an ideal point light source model in which the luminance value is inversely proportional to the square of the distance due to a positional deviation of the subject ST in the xy direction, an accuracy in measuring the three-dimensional shape of the subject ST by using the SFS technique can be improved.

Embodiment 3

In Embodiment 1, a scheme for setting the coefficient $\alpha$ in accordance with the height z of the subject ST has been described. In Embodiment 2, a scheme for setting the coefficient $\alpha$ in accordance with the position of the subject ST in the xy direction in a case in which the height z of the subject ST is fixed has been described.

In Embodiment 3, a scheme for setting the coefficient $\alpha$ in accordance with the height z of the subject ST and the position in the xy direction is described.

A basic configuration of a biometric authentication device 100 according to Embodiment 3 is the same as the configuration in Embodiment 1. However, there are slight differences between the configuration according to Embodiment 3 and the configuration according to Embodiment 1 in functions of a coefficient storage 31 and a coefficient setting unit 41C.

A coefficient storage 31 stores a function $F_\alpha(X,z)$ for calculating a coefficient $\alpha$ that corresponds to a set of a height z of a subject ST and a point X (pixel X) on a captured image.

In Embodiment 3, a coefficient setting unit 41C sets the coefficient $\alpha$ in accordance with the height z and the position in the xy direction of the subject ST. More specifically, the coefficient setting unit 41C specifies a region T in which the subject ST is located in the captured image in a well-known method, and calculates a mean value $\alpha_{AVE}$ of the coefficient $\alpha$ that corresponds to each of the pixels in the region T according to the following expression 50. In this case, a height z measured by a distance measuring unit 41C is used for the height z of the subject ST.

$$\alpha_{AVE} = \sum_{X \in T} F_\alpha(X, z)/N_T \qquad (50)$$

The coefficient setting unit 41C sets the calculated mean value $\alpha_{AVE}$ to be a coefficient $\alpha$ used to perform a luminance value correcting process and to measure a three-dimensional shape of the subject ST by using the SFS technique.

According to Embodiment 3, the biometric authentication device 100 sets the coefficient $\alpha$ on the basis of the height z and the position in the xy direction of the subject ST. By doing this, even when a guiding member that guides the position of the subject ST is not provided in the biometric authentication device 100, the coefficient $\alpha$ can be set in consideration of both the height z and the position in the xy direction of the subject ST.

Embodiment 4

In Embodiments 1 to 3, the biometric authentication device 100 itself includes the database 32, and has a function of collating feature data for collation with feature data for registration that has been registered in the database 32. In Embodiment 4, a biometric authentication system 1 that is configured of one or more biometric authentication sensors 70 and a server computer 80 is described as an example. All of Embodiments 1 to 3 can be applied to the biometric authentication system 1, but a case in which Embodiment 1 is applied to the biometric authentication system 1 is now described.

Figure 18:
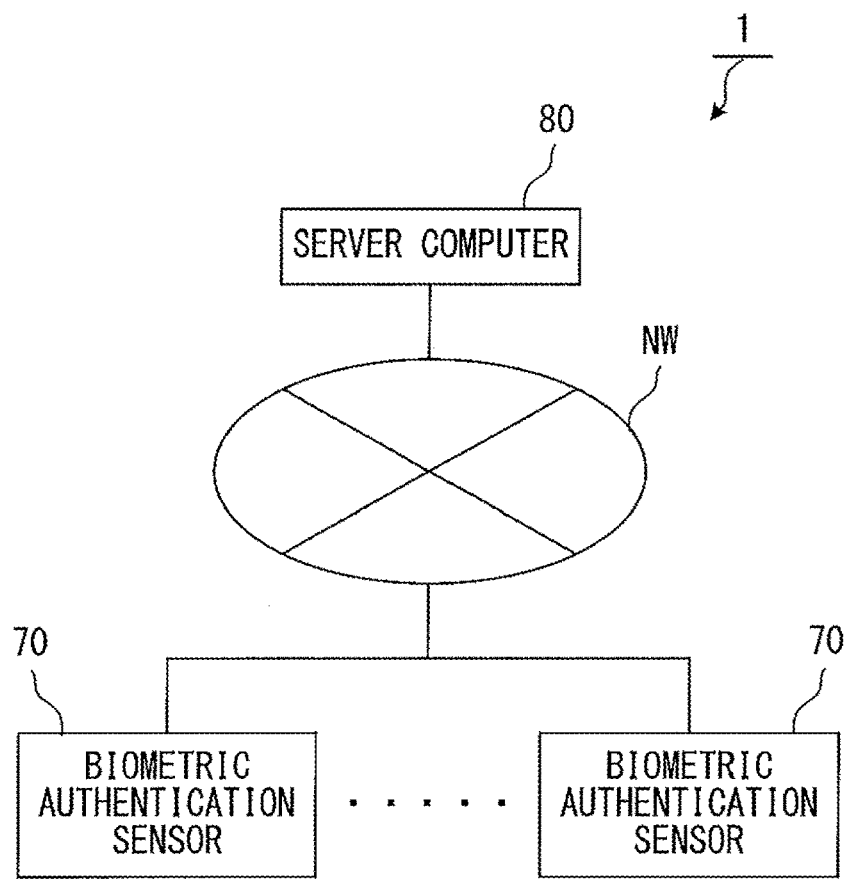
FIG. 18 illustrates an exemplary configuration of a biometric authentication system according to Embodiment 4.

FIG. 18 illustrates an exemplary configuration of the biometric authentication system 1 according to Embodiment 4. FIG. 19A is a functional block diagram illustrating an exemplary configuration of the biometric authentication sensor 70 in the biometric authentication system 1 according to Embodiment 4, and FIG. 19B is a functional block diagram illustrating an exemplary configuration of the server computer 80.

In the biometric authentication system 1 according to Embodiment 4, the one or more biometric authentication sensors 70 are communicably connected to the server computer 80 via a network NW, as illustrated in FIG. 18.

The biometric authentication sensor 70 according to Embodiment 4 includes an imaging unit 10, a distance sensor 20, a storage 30, a controller 40, and a communication unit 50, as illustrated in FIG. 19A. A basic configuration of the biometric authentication sensor 70 according to Embodiment 4 is the same as the configuration of the biometric authentication device 100 according to Embodiment 1. However, as illustrated in FIG. 19A, the biometric authentication sensor 70 according to Embodiment 4 is different from the biometric authentication device 100 according to Embodiment 1 in that the storage 30 of the biometric authentication sensor 70 does not function as the database 32 and that the controller 40 does not function as the collation processing unit 43. This is because a collation process is performed on the side of the server computer 80 in Embodiment 4. In addition, as illustrated in FIG. 19A, the biometric authentication sensor 70 according to Embodiment 4 is different from the biometric authentication device 100 according to Embodiment 1 in that the communication unit 50 is included.

The communication unit 50 includes, for example, a communication module and the like, and performs communication with the server computer 80. As an example, the communication unit 50 transmits feature data extracted by a feature extracting unit 42 to the server computer 80. As another example, the communication unit 50 receives a collation result transmitted from the server computer 80. The received collation result is stored in the data area of the storage 30 under the control of the controller 40.

The server computer 80 according to Embodiment 4 includes a communication unit 81, a storage 82, and a controller 83, as illustrated in FIG. 19B.

The communication unit 81 includes, for example, a communication module and the like, and performs communication with each of the biometric authentication sensors 70 in the biometric authentication system 1. As an example, the communication unit 81 receives feature data transmitted from the biometric authentication sensor 70. As another example, the communication unit 81 transmits a collation result of a collation processing unit 83A to the biometric authentication sensor 70 that is a transmitter of the feature data.

The storage 82 includes, for example, a RAM, a ROM, a Hard Disk Drive (HDD), and the like. The storage 82 functions as a work area of, for example, a CPU included in the controller 83, a program area in which various programs such as an operation program for controlling the entirety of the server computer 80 are stored, and a data area in which various types of data are stored. The storage 82 also functions as a database 82A, as illustrated in FIG. 19B.

The controller 83 includes, for example, a CPU and the like, and executes the operation program stored in the program area of the storage 82 so as to realize a function of the collation processing unit 83A, as illustrated in FIG. 19B. In addition, the controller 40 executes the operation program so as to perform processes such as a control program for controlling the entirety of the server computer 80.

Figure 20:
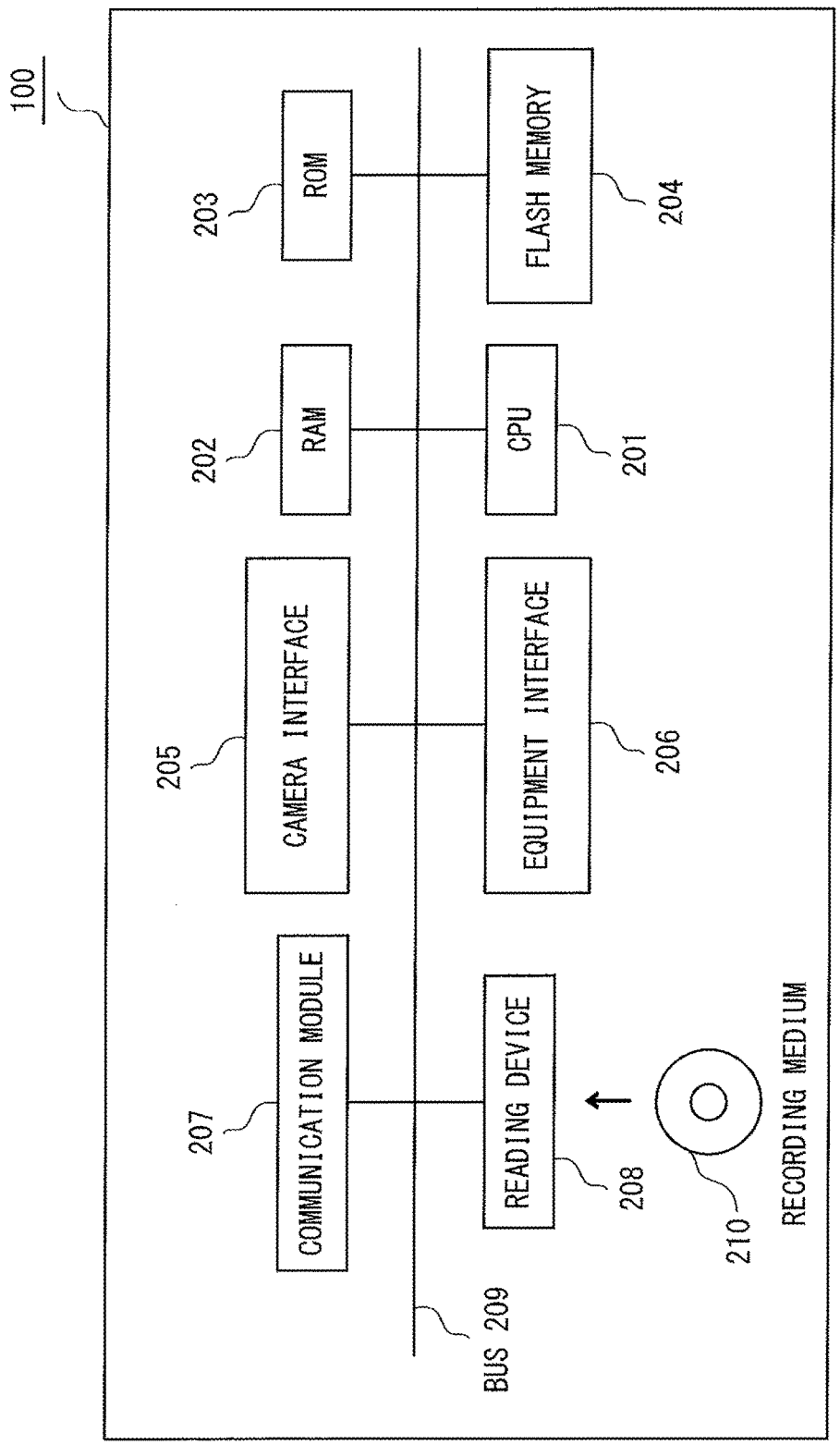
FIG. 20 illustrates an example of a hardware configuration of a biometric authentication device according to the embodiments.

FIG. 20 illustrates an example of a hardware configuration of the biometric authentication device 100 (or the biometric authentication sensor 70) according to the embodiments. The biometric authentication device 100 illustrated in FIG. 6 (or the biometric authentication sensor 70 illustrated in FIG. 19A) may be realized by various types of hardware illustrated in FIG. 20, for example. In the example of FIG. 20, the biometric authentication device 100 (or the biometric authentication sensor 70) includes a CPU 201, a RAM 202, a ROM 203, a flash memory 204, a camera interface 205 that connects an imaging device, an equipment interface 206 that connects the distance sensor 20 or the like, a communication module 207, and a reading device 208, and these pieces of hardware are connected to each other via a bus 209.

The CPU 201 loads an operation program stored, for example, in the flash memory 204 onto the RAM 202, and performs various processes while using the RAM 202 as a working memory. The CPU 201 can realize respective function units of the controller 40 illustrated in FIG. 6 and the like by executing the operation program.

The processes above may be performed by storing an operation program for performing the operations above in a computer-readable recording medium 210 such as a flexible disk, a Compact Disk-Read Only Memory (CD-ROM), a Digital Versatile Disk (DVD), or a Magneto Optical disk (MO) and distributing the operation program, and reading the operation program by the reading device 208 of the biometric authentication device 100 (or the biometric authentication sensor 70) and installing the operation program onto a computer. Further, an operation program may be stored in a disk drive or the like included in a server computer on the internet, and the operation program may be downloaded to a computer of the biometric authentication device 100 (or the biometric authentication sensor 70).

Depending on embodiments, a storage other than the RAM 202, the ROM 203, and the flash memory 204 may be used. As an example, the biometric authentication device 100 (or the biometric authentication sensor 70) may include a storage such as a Content Addressable Memory (CAM), a Static Random Access Memory (SRAM), or a Synchronous Dynamic Random Access Memory (SDRAM).

Depending on embodiments, a hardware configuration of the biometric authentication device 100 (or the biometric authentication sensor 70) may be different from the configuration illustrated in FIG. 20, and hardware having a standard or type other than that illustrated in FIG. 20 can be employed for the biometric authentication device 100 (or the biometric authentication sensor 70).

As an example, respective function units of the controller 40 of the biometric authentication device 100 (or the biometric authentication sensor 70) illustrated in FIG. 6 or the like may be realized by a hardware circuit. Specifically, the respective function units of the controller 40 illustrated in FIG. 6 or the like may be realized by a reconfigurable circuit such as a Field Programmable Gate Array (FPGA), an Application Specific Integrated Circuit (ASIC), or the like, instead of the CPU 201. Of course, these function units may be realized by both the CPU 201 and the hardware circuit.

Some embodiments and the variations thereof have been described above. However, the embodiments are not limited to the embodiments above, and are to be interpreted as including various variations and alternations of the embodiments above. As an example, it can be understood that various embodiments can be realized by deforming components without departing from the sprit or scope of the embodiments. It can also be understood that various embodiments can be implemented by appropriately combining a plurality of components disclosed in the embodiments above. Further, those skilled in the art could understand that various embodiments can be implemented by deleting or substituting some components of all of the components disclosed in the embodiment, or adding some components to the components disclosed in the embodiment.

All examples and conditional language provided herein are intended for the pedagogical purpose of aiding the reader in understanding the invention and the concepts contributed by the inventor to further the art, and are not to be construed as limitations to such specifically recited examples and conditions, nor does the organization of such examples in the specification related to a showing of the superiority and inferiority of the invention. Although one or more embodiments of the present invention have been described in detail, it should be understood that the various changes, substitutions, and alterations could be made hereto without departing from the spirit and scope of the invention.

What is claimed is:

1. A three-dimensional shape measuring device that measures a three-dimensional shape of a subject included in a captured image, the three-dimensional shape measuring device comprising
a processor configured:
to calculate, according to a position of the subject in the captured image, a coefficient that depends on a distance in a distance-dependent variable model from a light source to a measurement point of a luminance value according to a prescribed condition;
to calculate the luminance value by using the coefficient; and
to measure the three-dimensional shape of the subject according to the luminance value of the captured image and the coefficient, wherein
in calculating the coefficient, the processor specifies a region of the subject in the captured image, and calculates a mean value of an index that corresponds to each pixel included in the region to be the coefficient.

2. The three-dimensional shape measuring device according to claim 1, wherein
the processor configures
to estimate a reflectance of the subject according to the luminance value of a reference object that is a plane body for which a stored reflectance is constant and known, and the luminance value of the subject in the captured image, and performing, on the luminance value of the captured image, correction to make the reflectance of the subject almost equal to the reflectance of the reference object according to the estimated reflectance; and
to measure the three-dimensional shape of the subject according to the corrected luminance value of the captured image and the coefficient.

3. The three-dimensional shape measuring device according to claim 1, wherein
the processor configures
to perform, on the luminance value of the captured image, correction to remove influence of peripheral darkening on the luminance value of the captured image; and
to measure the three-dimensional shape of the subject according to the corrected luminance value of the captured image and the coefficient.

4. The three-dimensional shape measuring device according to claim 3, wherein
the processor configures to perform the correction to remove the influence of the peripheral darkening under the assumption that the index of the power of the distance from the light source to which the peripheral darkening is almost proportional is the coefficient.

5. The three-dimensional shape measuring device according to claim 1, wherein
the processor corrects a tilt of the subject in the captured image according to the three-dimensional shape of the subject.

6. A three-dimensional shape measuring method for measuring a three-dimensional shape of a subject included in a captured image, the three-dimensional shape measuring method comprising:
calculating, according to a position of the subject in the captured image, a coefficient that depends on a distance in a distance-dependent variable model from a light source to a measurement point of a luminance value according to a prescribed condition;
calculating the luminance value by using the coefficient; and
measuring the three-dimensional shape of the subject according to the luminance value of the captured image and the coefficient, wherein
in the calculating the coefficient, the three-dimensional shape measuring method includes specifying a region of the subject in the captured image, and calculating a mean value of an index that corresponds to each pixel included in the region to be the coefficient.

7. A non-transitory computer-readable recording medium having stored herein a program for causing a computer of a three-dimensional shape measuring device that measures a three-dimensional shape of a subject included in a captured image to execute a process comprising:
calculating, according to a position of the subject in the captured image, a coefficient that depends on a distance in a distance-dependent variable model from a light source to a measurement point of a luminance value according to a prescribed condition;
calculating the luminance value by using the coefficient; and
measuring the three-dimensional shape of the subject according to the luminance value of the captured image and the coefficient, wherein
in the calculating the coefficient, the process includes specifying a region of the subject in the captured image, and calculating a mean value of an index that corresponds to each pixel included in the region to be the coefficient.

* * * * *